US011026618B2

(12) United States Patent
Stewart et al.

(10) Patent No.: US 11,026,618 B2
(45) Date of Patent: Jun. 8, 2021

(54) INTRACARDIAC EGM SIGNALS FOR BEAT MATCHING AND ACCEPTANCE

(71) Applicant: Boston Scientific Scimed Inc., Maple Grove, MN (US)

(72) Inventors: Brian Stewart, North Reading, MA (US); Doron Harlev, Brookline, MA (US); Nathan H. Bennett, Cambridge, MA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 105 days.

(21) Appl. No.: 16/384,077

(22) Filed: Apr. 15, 2019

(65) Prior Publication Data
US 2019/0254554 A1  Aug. 22, 2019

Related U.S. Application Data

(63) Continuation of application No. 15/275,438, filed on Sep. 25, 2016, now Pat. No. 10,271,758.
(Continued)

(51) Int. Cl.
*A61B 5/00* (2006.01)
*A61B 5/35* (2021.01)
(Continued)

(52) U.S. Cl.
CPC .............. *A61B 5/35* (2021.01); *A61B 5/0245* (2013.01); *A61B 5/24* (2021.01); *A61B 5/287* (2021.01);
(Continued)

(58) Field of Classification Search
CPC . A61B 5/04012; A61B 5/0422; A61B 5/0432; A61B 5/04525; A61B 5/7203
See application file for complete search history.

(56) References Cited

U.S. PATENT DOCUMENTS

| 1,674,518 A | 6/1928 | Parsons |
| 2,939,309 A | 6/1960 | Sitton |

(Continued)

FOREIGN PATENT DOCUMENTS

| CN | 101156774 A | 4/2008 |
| CN | 103327887 A | 9/2013 |

(Continued)

OTHER PUBLICATIONS

Meininger et al., "Initial Experience with a Novel Focused Ultrasound Ablation System for Ring Ablation Outside the Pulmonary Vein", Journal of Interventional Cardiac Electrophysiology, 8:141-148, 2003.

(Continued)

*Primary Examiner* — Eric D. Bertram
(74) *Attorney, Agent, or Firm* — Faegre Drinker Biddle & Reath LLP

(57) ABSTRACT

A system for providing information about a patient's heart, the system including one or more catheters that receive intracardiac signals from electrical activity of the heart over one or more heart beat cycles and an electronic processor coupled to the one or more catheters. The electronic processor to: receive the intracardiac signals from the one or more catheters; preprocess the intracardiac signals to provide preprocessed signals, wherein each of the intracardiac signals is preprocessed to provide a corresponding preprocessed signal; and compare the preprocessed signals to a set of signals to determine a degree of similarity between each of the preprocessed signals and the set of signals.

15 Claims, 7 Drawing Sheets

Related U.S. Application Data

(60) Provisional application No. 62/233,341, filed on Sep. 26, 2015.

(51) Int. Cl.
*A61B 5/0245* (2006.01)
*A61B 5/24* (2021.01)
*A61B 5/287* (2021.01)
*A61B 5/316* (2021.01)
*A61B 5/333* (2021.01)
*A61B 5/339* (2021.01)

(52) U.S. Cl.
CPC .............. *A61B 5/316* (2021.01); *A61B 5/333* (2021.01); *A61B 5/339* (2021.01); *A61B 5/7203* (2013.01); *A61B 5/7475* (2013.01)

(56) References Cited

U.S. PATENT DOCUMENTS

| | | | |
|---|---|---|---|
| 4,649,924 A | 3/1987 | Taccardi | |
| 4,674,518 A | 6/1987 | Salo | |
| 4,840,182 A | 6/1989 | Carlson | |
| 4,920,490 A | 4/1990 | Isaacson | |
| 4,964,410 A | 10/1990 | Leahey et al. | |
| 5,156,151 A | 10/1992 | Imran | |
| 5,284,142 A | 2/1994 | Goble et al. | |
| 5,297,549 A | 3/1994 | Beatty et al. | |
| 5,300,068 A | 4/1994 | Rosar et al. | |
| 5,341,807 A | 8/1994 | Nardella | |
| 5,381,333 A | 1/1995 | Isaacson et al. | |
| 5,469,858 A | 11/1995 | Osborne | |
| 5,480,422 A | 1/1996 | Ben-Haim | |
| 5,500,011 A | 3/1996 | Desai | |
| 5,553,611 A | 9/1996 | Budd et al. | |
| 5,568,809 A | 10/1996 | Ben-Haim | |
| 5,577,502 A | 11/1996 | Darrow et al. | |
| 5,588,429 A | 12/1996 | Isaacson et al. | |
| 5,634,469 A | 6/1997 | Bruder et al. | |
| 5,662,108 A | 9/1997 | Budd et al. | |
| 5,687,737 A | 11/1997 | Branham et al. | |
| 5,697,377 A | 12/1997 | Wittkampf | |
| 5,704,365 A | 1/1998 | Albrecht et al. | |
| 5,711,305 A * | 1/1998 | Swanson .............. | A61B 5/0422 600/510 |
| 5,722,402 A | 3/1998 | Swanson et al. | |
| 5,724,985 A | 3/1998 | Snell et al. | |
| 5,810,740 A | 9/1998 | Paisner | |
| 5,840,025 A | 11/1998 | Ben-Haim | |
| 5,840,031 A | 11/1998 | Crowley | |
| 5,846,198 A | 12/1998 | Killmann | |
| 5,848,972 A | 12/1998 | Triedman et al. | |
| 5,921,982 A | 7/1999 | Lesh et al. | |
| 5,954,665 A | 9/1999 | Ben-Haim | |
| 5,971,933 A | 10/1999 | Gopakumaran et al. | |
| 5,983,126 A | 11/1999 | Wittkampf | |
| 6,014,581 A | 1/2000 | Whayne et al. | |
| 6,050,267 A | 4/2000 | Nardella et al. | |
| 6,095,150 A | 8/2000 | Panescu et al. | |
| 6,167,296 A | 12/2000 | Shahidi | |
| 6,226,542 B1 | 5/2001 | Reisfeld | |
| 6,236,883 B1 | 5/2001 | Ciaccio et al. | |
| 6,236,886 B1 | 5/2001 | Cherepenin et al. | |
| 6,240,307 B1 | 5/2001 | Beatty et al. | |
| 6,246,898 B1 | 6/2001 | Vesely et al. | |
| 6,254,536 B1 | 7/2001 | Devito | |
| 6,278,894 B1 | 8/2001 | Salo et al. | |
| 6,298,257 B1 | 10/2001 | Hall et al. | |
| 6,308,093 B1 | 10/2001 | Armoundas et al. | |
| 6,314,310 B1 | 11/2001 | Ben-Haim et al. | |
| 6,317,619 B1 | 11/2001 | Boernert et al. | |
| 6,318,375 B1 | 11/2001 | Plicchi et al. | |
| 6,360,123 B1 | 3/2002 | Kimchi et al. | |
| 6,368,285 B1 | 4/2002 | Osadchy et al. | |
| 6,400,981 B1 | 6/2002 | Govari | |
| 6,516,807 B1 | 2/2003 | Panescu et al. | |
| 6,547,082 B1 | 4/2003 | Babini | |
| 6,556,695 B1 | 4/2003 | Packer et al. | |
| 6,574,492 B1 | 6/2003 | Ben-Haim et al. | |
| 6,574,498 B1 | 6/2003 | Gilboa | |
| 6,593,884 B1 | 7/2003 | Gilboa et al. | |
| 6,599,241 B1 | 7/2003 | Murphy | |
| 6,600,948 B2 | 7/2003 | Ben-Haim et al. | |
| 6,603,996 B1 | 8/2003 | Beatty et al. | |
| 6,631,290 B1 | 10/2003 | Guck et al. | |
| 6,640,119 B1 | 10/2003 | Budd et al. | |
| 6,650,927 B1 | 11/2003 | Keidar | |
| 6,690,963 B2 | 2/2004 | Ben-Haim et al. | |
| 6,701,176 B1 | 3/2004 | Halperin et al. | |
| 6,728,562 B1 | 4/2004 | Budd et al. | |
| 6,773,402 B2 | 8/2004 | Govari et al. | |
| 6,807,439 B2 | 10/2004 | Edwards et al. | |
| 6,839,588 B1 | 1/2005 | Rudy | |
| 6,847,839 B2 | 1/2005 | Ciaccio et al. | |
| 6,872,428 B2 | 3/2005 | Yang et al. | |
| 6,892,090 B2 | 5/2005 | Verard et al. | |
| 6,892,091 B1 | 5/2005 | Ben-Haim et al. | |
| 6,939,309 B1 | 9/2005 | Beatty et al. | |
| 6,957,101 B2 | 10/2005 | Porath et al. | |
| 6,978,168 B2 | 12/2005 | Beatty et al. | |
| 6,990,370 B1 | 1/2006 | Beatty et al. | |
| 7,016,719 B2 | 3/2006 | Rudy et al. | |
| 7,043,292 B2 | 5/2006 | Tarjan et al. | |
| 7,263,397 B2 | 8/2007 | Hauck et al. | |
| 7,505,810 B2 | 3/2009 | Harlev et al. | |
| 7,515,954 B2 | 4/2009 | Harlev et al. | |
| 7,599,730 B2 | 10/2009 | Hunter et al. | |
| 7,706,867 B1 | 4/2010 | Ostrow | |
| 7,709,867 B2 | 5/2010 | Ishikawa et al. | |
| 7,729,752 B2 | 6/2010 | Harlev et al. | |
| 7,856,260 B1 | 12/2010 | Ryu | |
| 8,021,361 B2 | 9/2011 | Paul et al. | |
| 8,103,327 B2 | 1/2012 | Harlev et al. | |
| 8,103,338 B2 | 1/2012 | Harlev et al. | |
| 8,137,343 B2 | 3/2012 | Harlev et al. | |
| 8,182,433 B2 | 5/2012 | Leo et al. | |
| 8,267,926 B2 | 9/2012 | Paul et al. | |
| 8,357,152 B2 | 1/2013 | Govari et al. | |
| 8,428,700 B2 | 4/2013 | Harlev et al. | |
| 8,948,837 B2 | 2/2015 | Harlev et al. | |
| 9,002,442 B2 | 4/2015 | Harley et al. | |
| 9,107,599 B2 | 8/2015 | Harlev et al. | |
| 9,277,872 B2 | 3/2016 | Harlev et al. | |
| 9,289,148 B2 | 3/2016 | Harlev et al. | |
| 9,498,146 B2 | 11/2016 | Harlev et al. | |
| 9,888,862 B2 | 2/2018 | Harlev et al. | |
| 10,271,758 B2 * | 4/2019 | Stewart .................. | A61B 5/044 |
| 2001/0044578 A1 | 11/2001 | Ben-Haim et al. | |
| 2002/0055674 A1 | 5/2002 | Ben-Haim et al. | |
| 2002/0065455 A1 | 5/2002 | Ben-Haim et al. | |
| 2002/0091330 A1 | 7/2002 | MacAdam et al. | |
| 2002/0091333 A1 | 7/2002 | Hsu et al. | |
| 2002/0115941 A1 | 8/2002 | Whayne et al. | |
| 2002/0151807 A1 | 10/2002 | Goldin | |
| 2002/0161295 A1 | 10/2002 | Edwards et al. | |
| 2002/0177421 A1 | 11/2002 | Muhammad et al. | |
| 2003/0013958 A1 | 1/2003 | Govari et al. | |
| 2003/0018251 A1 | 1/2003 | Solomon | |
| 2003/0023130 A1 | 1/2003 | Ciaccio et al. | |
| 2003/0065271 A1 | 4/2003 | Khoury | |
| 2003/0072881 A1 | 4/2003 | Yang et al. | |
| 2003/0076277 A1 | 4/2003 | Muramatsu et al. | |
| 2003/0078509 A1 | 4/2003 | Panescu | |
| 2003/0120163 A1 | 6/2003 | Rudy et al. | |
| 2003/0176799 A1 | 9/2003 | Beatty et al. | |
| 2003/0216630 A1 | 11/2003 | Jersey-Willuhn et al. | |
| 2003/0236466 A1 | 12/2003 | Tarjan et al. | |
| 2004/0034300 A1 | 2/2004 | Verard et al. | |
| 2004/0039293 A1 | 2/2004 | Porath et al. | |
| 2004/0077942 A1 | 4/2004 | Hall et al. | |
| 2004/0097806 A1 | 5/2004 | Hunter et al. | |
| 2004/0127805 A1 | 7/2004 | MacAdam et al. | |
| 2004/0243015 A1 | 12/2004 | Smith et al. | |
| 2004/0254437 A1 | 12/2004 | Hauck et al. | |

(56) References Cited

U.S. PATENT DOCUMENTS

| | | |
|---|---|---|
| 2005/0038337 A1 | 2/2005 | Edwards |
| 2005/0054918 A1 | 3/2005 | Sra |
| 2005/0107834 A1 | 5/2005 | Freeman et al. |
| 2005/0154282 A1 | 7/2005 | Li et al. |
| 2005/0288599 A1 | 12/2005 | MacAdam et al. |
| 2006/0085049 A1 | 4/2006 | Cory et al. |
| 2006/0116575 A1 | 6/2006 | Willis |
| 2006/0122526 A1 | 6/2006 | Berenfeld et al. |
| 2006/0173251 A1 | 8/2006 | Govari et al. |
| 2006/0178587 A1 | 8/2006 | Khoury |
| 2006/0200049 A1 | 9/2006 | Leo et al. |
| 2006/0235476 A1 | 10/2006 | Gunderson et al. |
| 2006/0241401 A1 | 10/2006 | Govari et al. |
| 2007/0016007 A1 | 1/2007 | Govari et al. |
| 2007/0038078 A1 | 2/2007 | Osadchy |
| 2007/0049821 A1 | 3/2007 | Willis |
| 2007/0073179 A1 | 3/2007 | Afonso et al. |
| 2007/0083193 A1 | 4/2007 | Werneth et al. |
| 2007/0100332 A1 | 5/2007 | Paul et al. |
| 2007/0197929 A1 | 8/2007 | Porath et al. |
| 2007/0208260 A1 | 9/2007 | Afonso |
| 2007/0265539 A1 | 11/2007 | Hastings et al. |
| 2007/0270703 A1 | 11/2007 | He et al. |
| 2007/0287902 A1 | 12/2007 | Fuimaono et al. |
| 2007/0299351 A1* | 12/2007 | Harlev ............ A61B 34/20 600/509 |
| 2007/0299352 A1 | 12/2007 | Harlev et al. |
| 2007/0299353 A1 | 12/2007 | Harlev et al. |
| 2008/0137927 A1 | 6/2008 | Altmann et al. |
| 2008/0190438 A1 | 8/2008 | Harlev et al. |
| 2008/0221566 A1 | 9/2008 | Krishnan |
| 2008/0234588 A1 | 9/2008 | Feldman et al. |
| 2008/0249424 A1 | 10/2008 | Harlev et al. |
| 2008/0281319 A1 | 11/2008 | Paul et al. |
| 2009/0050948 A1 | 2/2009 | Ishikawa et al. |
| 2009/0069642 A1 | 3/2009 | Gao et al. |
| 2009/0069704 A1 | 3/2009 | MacAdam et al. |
| 2009/0093806 A1 | 4/2009 | Govari et al. |
| 2009/0099468 A1 | 4/2009 | Thiagalingam et al. |
| 2009/0171274 A1 | 7/2009 | Harlev et al. |
| 2009/0177072 A1 | 7/2009 | Harlev et al. |
| 2009/0253976 A1 | 10/2009 | Harlev et al. |
| 2009/0264767 A1 | 10/2009 | Griffin et al. |
| 2009/0281439 A1 | 11/2009 | Harlev et al. |
| 2010/0049069 A1 | 2/2010 | Tarassenko et al. |
| 2010/0106154 A1 | 4/2010 | Harlev et al. |
| 2010/0168620 A1 | 7/2010 | Klimovitch et al. |
| 2010/0274150 A1 | 10/2010 | Harlev et al. |
| 2010/0286550 A1 | 11/2010 | Harlev et al. |
| 2010/0286551 A1 | 11/2010 | Harlev et al. |
| 2010/0311482 A1 | 12/2010 | Lange |
| 2012/0184684 A1 | 7/2012 | Funk et al. |
| 2012/0184858 A1* | 7/2012 | Harlev ............ A61B 5/042 600/484 |
| 2012/0184863 A1 | 7/2012 | Harlev et al. |
| 2012/0184864 A1 | 7/2012 | Harlev et al. |
| 2012/0184865 A1 | 7/2012 | Harlev et al. |
| 2013/0109945 A1 | 5/2013 | Harlev et al. |
| 2014/0200430 A1* | 7/2014 | Spector ............ A61B 5/046 600/374 |
| 2015/0112178 A1 | 4/2015 | Harlev et al. |
| 2015/0196216 A1 | 7/2015 | Laughner et al. |
| 2015/0216438 A1 | 8/2015 | Bokan et al. |
| 2015/0282729 A1 | 10/2015 | Harlev et al. |
| 2016/0051160 A1 | 2/2016 | Harlev et al. |
| 2017/0042436 A1 | 2/2017 | Harlev et al. |
| 2017/0086701 A1 | 3/2017 | Stewart et al. |

FOREIGN PATENT DOCUMENTS

| | | |
|---|---|---|
| CN | 103718191 A | 4/2014 |
| EP | 0746229 B1 | 9/2003 |
| EP | 2663227 A1 | 11/2013 |
| EP | 2712546 A1 | 4/2014 |
| JP | 09-508293 A | 8/1997 |
| JP | 10-234693 A | 9/1998 |
| JP | 2001-070269 A | 3/2001 |
| JP | 2005-506097 A | 3/2005 |
| JP | 2005-131367 A | 5/2005 |
| JP | 2007-537823 A | 12/2007 |
| JP | 2008-536633 A | 9/2008 |
| JP | 2009-537252 A | 10/2009 |
| JP | 2009-539566 A | 11/2009 |
| WO | 2005/115232 A1 | 12/2005 |
| WO | 2006/113698 A1 | 10/2006 |
| WO | 2007/137077 A2 | 11/2007 |
| WO | 2010/020958 A1 | 2/2010 |
| WO | 2012/097067 A1 | 7/2012 |
| WO | 2014/186684 A1 | 11/2014 |

OTHER PUBLICATIONS

Merrill, Daniel R. et al., "Electrical stimulation of excitable tissue: design of efficacious and safe protocols", Journal of Neuroscience Methods, 141:171-198, 2005.

Miller, "Editor's Forum—Application of Registration for Ablation: A Marriage of Technologies", Journal of Interventional Cardiac Electrophysiology, 11:87-89, 2004.

Nademanee et al., "A New Approach for Catheter Ablation of Atrial Fibrillation: Mapping of the Electrophysiologic Substrate", Journal of the American College of Cardiology, 43(11):2044-2053, 2004.

Noseworthy et al., "The Impact of Respiration on Left Atrial and Pulmonary Venous Anatomy: Implications for Image-Guided Intervention", Heart Rhythm, 2:1173-1178, 2005.

Pappone et al., "Robotic Magnetic Navigation for Atrial Fibrillation Ablation", Journal of the American College of Cardiology, 47(7): 1390-1400, 2006.

Paragios, "A Level Set Approach for Shape-Driven Segmentation and Tracking of the Left Ventricle", IEEE Transactions on Medical imaging, 22(6):773-776, 2003.

Persson et al., "A Simple Mesh Generator in MATLAB", SIAM Review, 46(2):329-345, 2004.

Persson, Per-Olof. "Mesh Generation for Implicit Geometries." Massachusetts Institute of Technology, Thesis, Feb. 2005, 126 pages.

Pham, Dzung, et al., "Current Methods in Medical Image Segmentation", Annu. Rev. Biomed. Eng., 02:315-337, 2000.

Rao et al., "Novel Noncontact Catheter System for Endocardial Electrical and Anatomical Imaging", Annals of Biomedical Engineering, 32(4):573-584, 2004.

Reddy et al., "Integration of Cardiac Meagnetic Resonance Imaging with Three-Dimentional Electroanatomic Mapping to Guide Left Ventricular Catheter Manipulation—Feasibility is a Porcine Modelof Healed Myocardial Infarction", Journal of the American College of Cardiology, 44(11):2202-2213, 2004.

Reddy et al., "Use of a Diode Laser Balloon Ablation Catheter to Generate Circumferential Pulmonary Venous Lesions in an Open-Thoracotomy Caprine Model", PACE, 27:52-57, 2004.

Sanders et al., "Spectral Analysis Identifies Sites of High-Frequency Activity Maintaining Atrial Fibrillation in Humans", Circulation, 112:789-797, 2005.

Sethian, "Level Set Methods and Fast Marching Methods: Evolving Interfaces in Computational Geometry, Fluid Mechanics, Computer Vision, and Materials Science", Department of Mathematics—University of California, Berkeley, Cambridge University Press, 1999.

Smits et al., "Catheter-Based Intramyocarial Injection of Autologous Skeletal Myoblasts as a Primary Treatment of Ischemic Heart Failure", Journal of the American College of Cardiology, 42(12):2063-2069, 2003.

Solomon et al., "Real-Time Cardiac Catheter Navigation on Three-Dimensional CT Images", Journal of Interventional Cardiac Electrophysiology, 8:27-36, 2003.

Sra et al., "Registration of Three-Dimensional Left Atrial Computed Tomographic Images With Projection Images Obtained Using Fluoroscopy", Circulation, 112:3763-3768, 2005.

(56) References Cited

OTHER PUBLICATIONS

Sra, Jasbir et al, "Registration of 3D Computed Tomographic Images With Interventional Systems: Implications for Catheter Ablation of Atrial Fibrillation", J Interv Card Electrophysiol, 16:141-148, 2006.
Stevenson, "Radiofrequency Catheter Ablation of Ventricular Tachycardia After Myocardial Infarction", Circulation, 98:308-314, 1998.
Taccardi et al., "A New Intracavitary Probe for Detecting the Site of the Origin of Ectopic Ventricular Beats During One Cardiac Cycle", Circulation, 75(1):272-281, 1987.
Thal et al., "Novel Applications in Catheter Ablation", Journal of Interventional Cardiac Electrophysiology, 13:17-21, 2005.
Thiagalingam et al., "Noncontact Mapping of the Left Ventricle: Insights from Validation With Transmural Contact Mapping", PACE, 27:570-578, 2004.
U.S. Appl. Harlev et al., filed Jan. 13, 2011., U.S. Appl. No. 61/432,404, U.S. Appl. No. 61/432,404.
Voth, "The Inverse Problem of Electrocardiography: Industrial Solutions and Simulations", BEM and NFSI Conference Proceedings, Minneapolis, MN, May 12-15, 2005, pp. 191-194.
Wazni et al., "Atrial Arrhythmias After Surgical Maze", Journal of the American College of Cardiology, Elsevier, New York, NY, vol. 48, No. 7, Oct. 3, 2006, pp. 1405-1409.
Wittkampf et al., "LocaLisa: New Technique for Real-Time 3-Dimensional Localization of Regular Intracardiac Electrodes", Circulation, 99:1312-1317, 1999.
Yezzi, Anthony et al., "A Geometric Snake Model for Segmentation", IEEE Transactions on Medical Imaging, 16(2) Apr. 1997.
Adams et al., "Seeded Region Growing", IEEE Transactions on Pattern Analysis and Machine Intelligence, 16(6):641-647, 1994.
Arthur, "Clinical Use of Intracardiac Impedance: Current Applications and Future Perspectives", PACE, vol. 24:500-506, Apr. 2001.
Authorized officer Blaine R. Copenheaver, International Search Report/Written Opinion in PCT/US2012/020935 dated May 8, 2012, 30 pages.
Authorized officer Carl H. Layno, International Search Report and the Written Opinion in PCT/US07/70854 dated Sep. 12, 2008, 15 pages.
Authorized officer, Blaine R. Copenheaver, International Search Report and the Written Opinion in PCT/US2009/061277 dated Apr. 8, 2010, 13 pages.
Baan, Jan et al., "Continuous Measurement of Left Ventricular Volume in Animals and Humans by Conductance Catheter", Circulation, 07(5):812-823, 1984.
Badics, "Real-Time Reconstruction of Endocardial Potential Maps in Non-Contact Cardiace Mapping", International Journal for computation and Mathematics in Electrical Engineering (COMPEL), vol. 28, No. 4, 2009.
Ben-Haim et al., "Nonfluoroscopic, in Vivo Navigation and Mapping Technology", Nature Medicine, 2(12):1393-1395, 1996.
Besl et al., "A Method for Registration of 3-D Shapes", IEEE Transaction on Pattern Analysis and Machine Intelligence, 14(2):239-256, 1992.
Blomstrom-Lundqvist et al., "ACC/AHA/ESC Guidelines for the Management of Patients with Supraventricular Arrhythmias-Executive Summary", Journal of the American College of Cardiology, 42(8):1493-1531, 2003.
Breithardt et al., "AHA Medical/Scientific Statement—Special Report: Standards for Analysis of Ventricular Late Potentials Using High-Resolution or Signal/Averaged Electrocardiography", Circulation, 83(4):1481-1488, 1991.
Brooks et al., "Electrical Imaging of the Heart", IEEE Signal Processing Magazine, pp. 24-42, 1997.
Caspi et al., "Stem Cell Research: Regenerating the Heart Using Human Embryonic Stem Cells—from Cell to Bedside", IMAJ 8:208-214, 2006.
Cheney, Margaret, et al. "Electrical Impedance Tomography." Society for Industrial and Applied Mathematics, Review, 41(1):85-101, Mar. 1999.
De Groot et al., "Three-Dimensional Catheter Positioning During Radiofrequency Ablation in Patients: First Application of a Real-Time Position Management System", Journal of Cardiovascular Electrophysiology, 11:1183-1192, 2000.
Donahue et al., "Focal Modification of Electrical Conduction in the Heart by Viral Gene Transfer", Nature Medicine, 6(12):1395-1398, 2000.
Dong et al., "Integrated Electroanatomic Mapping With Three-Dimensional Computed Tomographic Images for Real-Time Guided Ablations", Circulation 113:186-194, 2006.
Durrer et al., "Total Excitation of the Isolated Human Heart", Circulation, XL1:899-912, 1970.
Ector, Joris et al., "Cardiac Three-Dimensional Magnetic Resonance Imaging and Fluoroscopy Merging", Circulation, 112:3769-3776, 2005.
Extended International Search Report issued in European application 12733844.0, dated Jun. 26, 2017, 9 pages.
Extended International Search Report issued in European Application 12734224.4, dated Jun. 27, 2017, 10 pages.
Friedman, "Catheter Cryoablation of Cardiac Arrhythmias", Current Opinion in Cardiology, 20:48-54, 2005.
Friedman, "Novel Mapping Techniques for Cardiac Electrophysiology", Heart, 87:575-582, 2002.
Geddes, L.A. et al., "Criteria for the Selection of Materials for implanted Electrodes", Annals of Biomedical Engineering, vol. 31, pp. 879-890 (2003).
Gepstein et al., "A Novel Method for Nonfluoroscopic Catheter-Based Electroanatomical Mapping of the Heart", Circulation 95:1611-1622, 1997.
Haug. E J. et al.: Design Sensitivity Analysis of Structural Systems, Mathematics in Science and Engineering, vol. 177 (1986).
Huang, Yi-Chih et al., "Development of a Third Generation Intraventricular Impedance Imaging (EI) System Evaluation of Hardware Design", Engineering in Medicine and Biology Society, Proceedings of the 19th Annual International Conference of the IEEE/EMBS, 6:2442-2444 Oct. 30-Nov. 2, 1997.
International Search Report and Written Opinion issued in PCT/US2008/052385, dated Aug. 8, 2008, 6 pages.
International Search Report and Written Opinion issued in PCT/US2009/036099, dated Apr. 28, 2009, 21 pages.
International Search Report and Written Opinion issued in PCT/US2009/061277, dated Apr. 8, 2010, 13 pages.
International Search Report and Written Opinion issued in PCT/US2016/053627, dated Feb. 14, 2017, 17 pages.
Jain et al., "Cell Therapy Attenuates Deleterious Ventricular Remodeling and Improves Cardiac Performance after Myocardial Infarction", Circulation, 103:1920-1927, 2001.
Jalife, "Rotors and Spiral Waves in Atrial Fibrillation", Journal of Cardiovascular Electrophysiology, 14:776-780, 2003.
Jane et al., "Alignment Methods for Averaging of High-Resolution Cardiac Signals: A Comparative Study of Performance", IEEE Transactions on Biomedical Engineering, 38(6):571-579, 1991.
Jia et al., "Electrophysiologic Endocardial Mapping from a Noncontact Nonexpandable Catheter: A Validation Study of a Geometry-Based Concept". Journal of Cardiovascular Electrophysiology, 11:1238-1251, 2000.
Ju et al., "Mean value coordinates for closed triangular meshes," ACM Trans. Graph. 24(3):561-566 (2005).
Kikuchi et al., "Targeted Modification of Atrial Electrophysiology by Homogeneous Transmural Artial Gene Transfer", Circulation, 111:264-270, 2005.
Kistler et al., "Validation of Three-Dimensional Cardiac Image Integration: Use of Integrated CT Image into Electroanatomic Mapping System to Performa Catheter Ablation of Atrial Fibrillation", Journal of Cardiovascular Electrophysiology, 17:341-348, 2006.
Kriebel et al., "Noncontact Mapping and Radiofrequency Catheter Ablation of Fast and Hemodynamically Unstable Ventricular Tachycardia After Surgical Repair of Tetralogy of Fallot", Journal of the

(56) References Cited

OTHER PUBLICATIONS

American College of Cardiology, Elsevier, New York, NY, vol. 50, No. 22, Nov. 13, 2007, pp. 2162-2168.

Kuklik et al., "The reconstruction, from a set of points, and analysis of the interior surface of the heart chamber", Physiol. Meas. 25:617-627, 2004.

Kun, Stevan et al., "Conductance Volumetric Model of an Eccentrically Positioned Catheter within a Three-Compartment Ellipsoidal Ventricle", U, IEEE Transactions on Jun. 1993, 40(6); 589-592.

L. Piegl, W. Tiller. The NURBS Book, 2nd Edition, Springer (1997).

Laciar et al., "Improved Alignment Method for Noisy High-Resolution ECG and Holter Records Using Multiscale Cross-Correlation", IEEE Transactions on Biomedical Engineering, 50(3):344-353, 2003.

Liu et al., "Endocardial Potential Mapping from a Noncontact Nonexpandable Catheter: A Feasibility Study", Annals of Biomedical Engineering, 26:994-1009, 1998.

Lorensen et al., "Marching Cubes: A High Resolution 3D Surface Construction Algorithm", Computer Graphics 21(4):163-169, Jul. 1987.

Makela et al., "A Review of Cardiac Image Registration Methods", IEEE Transaction on Medical Imaging, 21(9):1011-1021, 2002.

Malladi, R.et al., "A Geometric Approach to Segmentation and Analysis of 3D Medical Images", Mathematical Methods in Biomedical Image Analysis, Proceedings of the Workshop on, Jun. 21-22, 1996, pp. 244-252.

Mangan, Alan et al., "Partitioning 3D Surface Meshes Using Watershed Segmentation", IEEE Transactions on Visualization and Computer Graphics, 5(4):308-321, 1999.

Martin K. Stiles et al., "The Effect of Electrogram Duration on Quantification of Complex Fractionated Atrial Electrograms and Dominant Frequency", Journal of Cardiovascular Electrophysiology, vol. 19, No. 3, Mar. 1, 2008, pp. 252-258.

McLeish et al., "A Study of the Motion and Deformation of the Heart Due to Respiration," IEEE Transactions on Medical Imaging, 21(9):1142-1150 (2002).

\* cited by examiner

INTRACARDIAC EGM SIGNALS FOR BEAT MATCHING AND ACCEPTANCE

CROSS-REFERENCE TO RELATED APPLICATION

This application is a Continuation Application of the application Ser. No. 15/275,438, filed Sep. 25, 2016, now U.S. Pat. No. 10,271,758, which claims priority to Provisional Application No. 62/233,341, filed Sep. 26, 2015, which is herein incorporated by reference in its entirety.

TECHNICAL FIELD

This disclosure relates to systems and methods for providing information about a patient's heart and, in particular, to systems and methods for electro-anatomically mapping the patient's heart.

BACKGROUND

Use of minimally invasive procedures, such as catheter ablation, to treat a variety of heart conditions, such as supraventricular and ventricular arrhythmias, is becoming increasingly prevalent. Often, these procedures involve the mapping of electrical activity in the heart at various locations on the endocardial or epicardial surface, referred to as cardiac mapping, to identify the mechanism of the arrhythmia followed by a targeted ablation of the site. To perform the cardiac mapping, a catheter with one or more electrodes can be inserted into the patient's heart.

Cardiac mapping techniques include contact mapping, near contact mapping, and non-contact mapping. In contact mapping, one or more catheters are advanced into the heart and physiological signals resulting from the electrical activity of the heart are acquired with one or more electrodes located at the catheter distal tip after determining that the tip is in stable and steady contact with the endocardial surface of a heart chamber. The location and electrical activity can be measured on a point-by-point basis at, for example, about 50 to 200 points on the internal surface of the heart to construct an electro-anatomical depiction of the heart. In near-contact mapping, a movable catheter having multiple spatially distributed electrodes is placed in a heart chamber of interest and moved to one or more locations within the chamber of interest, where the electrodes are on or near, such as within millimeters of, the endocardial surface of the heart chamber. Measurements are taken automatically at each of the locations of the catheter, without determining whether the electrodes are in contact with the surface of the heart. These measurements are analyzed to detect the endocardial surface of the heart chamber in the vicinity of the catheter. The location of the catheter, e.g., a location provided by a tracking system, and the measurements from the electrodes are used to reconstruct the chamber anatomy, where, for example, 20,000 measurements may be made to construct an electro-anatomical depiction of the heart. As the tracked catheter is moved inside the chamber, a partial or complete representation of the chamber anatomy can be constructed. In non-contact mapping, a multiple electrode catheter is placed in the heart chamber of interest and the catheter is deployed to assume a three dimensional shape. Using the signals detected by the non-contact electrodes and information on chamber anatomy and relative electrode location, the system calculates and provides physiological information regarding the endocardial surface of the heart chamber. In either cardiac mapping technique, the generated map may then serve as the basis for deciding on a therapeutic course of action, such as tissue ablation, to alter the propagation of the heart's electrical activity and to restore normal heart rhythm.

During cardiac mapping of a patient's heart, the mapping process determines whether a cardiac beat matches a target beat morphology. If the cardiac beat matches the target beat morphology, the signals obtained in conjunction with the cardiac beat can be mapped into a map dataset for the target beat morphology. If the cardiac beat does not match the target beat morphology, the signals obtained in conjunction with the cardiac beat may be discarded. Often, electrocardiogram (ECG) signals are used to detect the similarity between the cardiac beat and the target beat morphology. However, the industry is continuously developing new and improved systems and methods for cardiac mapping.

SUMMARY

Example 1 is a system for providing information about a patient's heart. The system includes one or more catheters that receive intracardiac signals from electrical activity of the heart over one or more heart beat cycles. The system being characterized by an electronic processor coupled to the one or more catheters to: receive the intracardiac signals from the one or more catheters; preprocess the intracardiac signals to provide preprocessed signals, wherein each of the intracardiac signals is preprocessed to provide a corresponding preprocessed signal; and compare the preprocessed signals to a set of signals to determine a degree of similarity between each of the preprocessed signals and the set of signals.

Example 2 is the system of Example 1, wherein to preprocess the intracardiac signals the electronic processor is to: apply a transform function to the intracardiac signals to provide transformed signals, wherein each of the intracardiac signals is transformed to a corresponding transformed signal; and apply a morphological close operation to each of the transformed signals to reduce noise in the preprocessed signals.

Example 3 is the system of Example 2, wherein the transform function is a Hilbert transform and the close operation is a non-boolean close operation.

Example 4 is the system of any of Examples 1-3, wherein the electronic processor is to: detect a beat of the heart; define a window for samples of the intracardiac signals based on the beat; and provide a matrix of the samples of the intracardiac signals in the window.

Example 5 is the system of any of Examples 1-4, wherein the one or more catheters include one or more reference catheters situated at stable positions in the patient's body and the set of signals includes a template of signals determined from the intracardiac signals received by the one or more reference catheters.

Example 6 is the system of any of Examples 1-5, wherein to compare the preprocessed signals the electronic processor is to: receive individual threshold values for each of the intracardiac signals; set a master threshold value; provide dynamic threshold values for each of the intracardiac signals based on the individual threshold values and the master threshold value; compare the preprocessed signals to the set of signals to obtain comparison values for the intracardiac signals; and compare the comparison values to the dynamic threshold values to determine whether a beat of the intracardiac signals is to be accepted into an existing cardiac map.

Example 7 is the system of any of Examples 1-6, wherein to compare the preprocessed signals the electronic processor is to: receive individual threshold values for each of the intracardiac signals; compare the preprocessed signals to the set of signals to obtain comparison values for the intracardiac signals; and compare the comparison values to the individual threshold values to determine whether a beat of the intracardiac signals is to be accepted.

Example 8 is the system of any of Examples 1-7, wherein to compare the preprocessed signals the electronic processor is to: receive individual threshold values for each of the intracardiac signals; and compare each of the individual threshold values to a fixed value and if all of the individual threshold values are less than the fixed value, accept one or more beats of the intracardiac signals.

Example 9 is the system of any of Examples 1-8, wherein the one or more catheters include one or more mapping catheters positioned in the patient's heart and the set of signals includes a set of signals from the one or more mapping catheters and a previously detected beat of the heart.

Example 10 is the system of any of Examples 1-9, wherein to compare the preprocessed signals the electronic processor is to: compare the preprocessed signals to the set of signals from the one or more mapping catheters and a previously detected beat of the heart to obtain previous beat comparison values; and compare each of the previous beat comparison values to a corresponding threshold value to determine whether a beat of the intracardiac signals is to be accepted.

Example 11 is the system of any of Examples 1-10, wherein the electronic processor is to determine whether to accept the intracardiac signals into a cardiac map based on the degree of similarity, and the electronic processor is to: classify the intracardiac signals into a current existing cardiac map; classify the intracardiac signals into another existing cardiac map; or make a new cardiac map based on the intracardiac signals.

Example 12 is a method for mapping a patient's heart. The method includes receiving intracardiac signals from electrical activity of the heart over one or more heart beat cycles at one or more catheters. The method being characterized by the steps of: receiving the intracardiac signals at an electronic processor that is coupled to the one or more catheters; preprocessing the intracardiac signals, by the electronic processor, to provide preprocessed signals, wherein each of the intracardiac signals is preprocessed to provide a corresponding preprocessed signal; and comparing the preprocessed signals, by the electronic processor, to a set of signals to determine a degree of similarity between each of the preprocessed signals and the set of signals.

Example 13 is the method of Example 12, wherein preprocessing the intracardiac signals includes: transforming each of the intracardiac signals via a transform function; and applying a morphological close operation to reduce noise in the preprocessed signals.

Example 14 is the method of any of Examples 12 and 13, wherein the one or more catheters include one or more reference catheters situated at stable positions in the patient's body and the set of signals includes a template of signals determined from the intracardiac signals received by the one or more reference catheters.

Example 15 is the method of any of Examples 12-14, wherein the one or more catheters include one or more mapping catheters positioned in the patient's heart and the set of signals includes a set of signals from the one or more mapping catheters and a previously detected beat of the heart.

Example 16 is a system for providing information about a patient's heart. The system includes one or more catheters that receive intracardiac signals from electrical activity of the heart over one or more heart beat cycles and an electronic processor coupled to the one or more catheters. The electronic processor to: receive the intracardiac signals from the one or more catheters; preprocess the intracardiac signals to provide preprocessed signals, wherein each of the intracardiac signals is preprocessed to provide a corresponding preprocessed signal; compare the preprocessed signals to a set of signals to determine a degree of similarity between each of the preprocessed signals and the set of signals; and determine whether to accept one or more beats of the intracardiac signals into an existing cardiac map based on the degree of similarity.

Example 17 is the system of Example 16, wherein to preprocess the intracardiac signals the electronic processor is to: apply a transform function to the intracardiac signals to provide transformed signals, wherein each of the intracardiac signals is transformed to a corresponding transformed signal; and apply a morphological close operation to each of the transformed signals to reduce noise in the preprocessed signals.

Example 18 is the system of Example 17, wherein the transform function is a Hilbert transform and the close operation is a non-boolean close operation.

Example 19 is the system of Example 16, wherein the electronic processor is to: detect a beat of the heart; define a window for samples of the intracardiac signals based on the beat; and provide a matrix of the samples of the intracardiac signals in the window.

Example 20 is the system of Example 16, wherein the one or more catheters include one or more reference catheters situated at stable positions in the patient's body and the set of signals includes a template of signals determined from the intracardiac signals received by the one or more reference catheters.

Example 21 is the system of Example 16, wherein the one or more catheters include one or more mapping catheters positioned in the patient's heart and the set of signals includes a set of signals from the one or more mapping catheters and a previously detected beat of the heart.

Example 22 is the system of Example 16, wherein to compare the preprocessed signals the electronic processor is to: receive individual threshold values for each of the intracardiac signals; set a master threshold value; provide dynamic threshold values for each of the intracardiac signals based on the individual threshold values and the master threshold value; compare the preprocessed signals to the set of signals to obtain comparison values for the intracardiac signals; and compare the comparison values to the dynamic threshold values to determine whether a beat of the intracardiac signals is to be accepted into an existing cardiac map.

Example 23 is the system of Example 16, wherein to compare the preprocessed signals the electronic processor is to: receive individual threshold values for each of the intracardiac signals; compare the preprocessed signals to the set of signals to obtain comparison values for the intracardiac signals; and compare the comparison values to the individual threshold values to determine whether a beat of the intracardiac signals is to be accepted into an existing cardiac map.

Example 24 is the system of Example 16, wherein to compare the preprocessed signals the electronic processor is to: receive individual threshold values for each of the intracardiac signals; and compare each of the individual threshold values to a fixed value and if all of the individual threshold values are less than the fixed value, accept one or more beats of the intracardiac signals into an existing cardiac map.

Example 25 is the system of Example 16, wherein to compare the preprocessed signals the electronic processor is to: compare the preprocessed signals to a set of signals from one or more mapping catheters and a previously detected beat of the heart to obtain previous beat comparison values; and compare each of the previous beat comparison values to a corresponding threshold value to determine whether a beat of the intracardiac signals is to be accepted.

Example 26 is the system of Example 16, wherein the electronic processor is to determine whether to: classify the intracardiac signals into the current cardiac map; classify the intracardiac signals into another existing cardiac map; or make a new cardiac map based on the intracardiac signals.

Example 27 is a system for providing information about a patient's heart. The system includes one or more catheters that receive intracardiac signals from electrical activity of the heart over one or more heart beat cycles and an electronic processor coupled to the one or more catheters. The electronic processor to receive the intracardiac signals from the one or more catheters and preprocess the intracardiac signals to provide preprocessed signals, wherein the electronic processor is to apply a transform function to the intracardiac signals to provide transformed signals, wherein each of the intracardiac signals is transformed to a corresponding transformed signal and apply a close operation to each of the transformed signals to reduce noise in the preprocessed signals. Also, the electronic processor is to correlate the preprocessed signals to a set of signals to determine a degree of correlation between each of the preprocessed signals and the set of signals and determine whether to accept the intracardiac signals into an existing cardiac map based on the degree of correlation.

Example 28 is the system of Example 27, wherein the one or more catheters include one or more reference catheters situated at stable positions in the patient's body and the set of signals includes a template of signals determined from the intracardiac signals received by the one or more reference catheters.

Example 29 is the system of Example 27, wherein the one or more catheters include one or more mapping catheters positioned in the patient's heart and the set of signals includes a set of signals from the one or more mapping catheters and a previously detected beat of the heart.

Example 30 is a method for mapping a patient's heart. The method including: receiving intracardiac signals from electrical activity of the heart over one or more heart beat cycles at one or more catheters; receiving the intracardiac signals at an electronic processor that is coupled to the one or more catheters; preprocessing the intracardiac signals, by the electronic processor, to provide preprocessed signals, wherein each of the intracardiac signals is preprocessed to provide a corresponding preprocessed signal; comparing the preprocessed signals, by the electronic processor, to a set of signals to determine a degree of similarity between each of the preprocessed signals and the set of signals; and determining whether to accept the intracardiac signals into an existing cardiac map based on the degree of similarity.

Example 31 is the method of Example 30, wherein preprocessing the intracardiac signals includes transforming each of the intracardiac signals via a transform function and applying a close operation to reduce noise in the preprocessed signals.

Example 32 is the method of Example 30, wherein comparing the preprocessed signals comprises: receiving individual threshold values for each of the intracardiac signals; setting a master threshold value; providing dynamic threshold values for each of the intracardiac signals based on the individual threshold values and the master threshold value; comparing the preprocessed signals to the set of signals to obtain comparison values for the intracardiac signals; and comparing the comparison values to the dynamic threshold values to determine whether a beat of the intracardiac signals is to be accepted into an existing cardiac map.

Example 33 is the method of Example 30, wherein comparing the preprocessed signals comprises: receiving individual threshold values for each of the intracardiac signals; comparing the preprocessed signals to the set of signals to obtain comparison values; and comparing the comparison values to the individual threshold values to determine whether a beat of the intracardiac signals is to be accepted into an existing cardiac map.

Example 34 is the method of Example 30, wherein comparing the preprocessed signals comprises: receiving individual threshold values for each of the intracardiac signals; and comparing each of the individual threshold values to a fixed value and if all of the individual threshold values are less than the fixed value, accept one or more beats of the intracardiac signals into an existing cardiac map.

Example 35 is the method of Example 30, wherein comparing the preprocessed signals comprises: comparing the preprocessed signals to a set of signals from one or more mapping catheters and a previously detected beat of the heart to obtain previous beat comparison values; and comparing each of the previous beat comparison values to a corresponding threshold value to determine whether a beat of the intracardiac signals is to be accepted.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1:
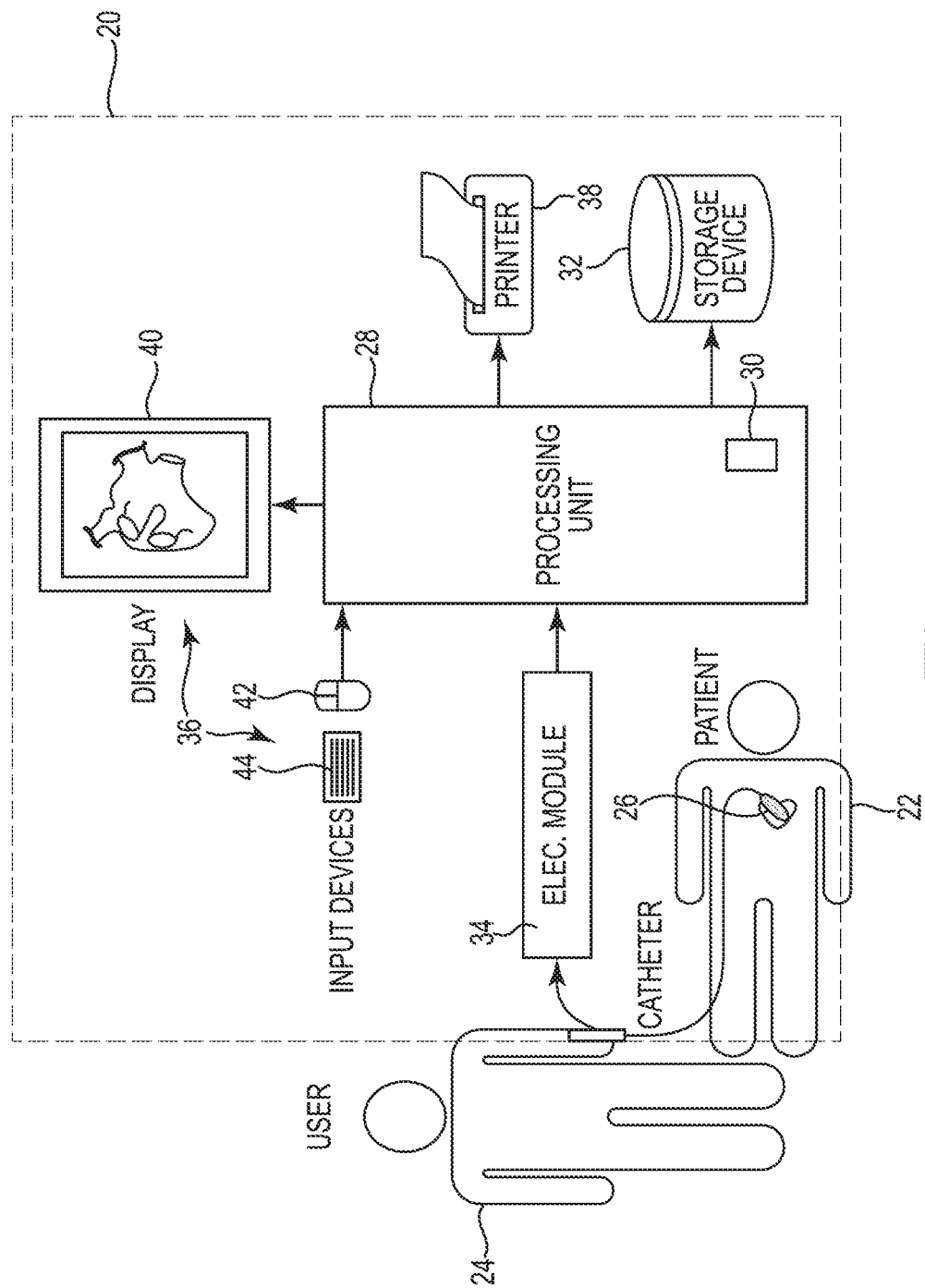
FIG. 1 is a diagram illustrating an electro-anatomical mapping system for mapping cardiac rhythms of a patient, according to embodiments of the disclosure.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

The present disclosure describes systems and methods that use intracardiac electrogram (EGM) signals for detecting and processing cardiac beats. The detected and processed beats can be compared to target beat morphologies, accepted into map datasets, and/or classified into different cardiac beat morphologies. This beat detection and processing includes beat detection, beat comparison, and beat classification that uses metrics derived from comparing the incoming intracardiac EGM signals to another set of intracardiac EGM signals. In some embodiments, the other set of intracardiac EGM signals includes a template of intracardiac EGM signals. In some embodiments, the other set of intracardiac EGM signals includes a set of intracardiac EGM signals obtained from a previous cardiac beat, such as the most recent previous cardiac beat.

Embodiments of the systems and methods described herein may add signals to selected cardiac beat morphologies, check for consistencies between neighboring cardiac beats, and/or automatically classify the cardiac beats into different cardiac beat morphologies. Embodiments of systems and methods described herein may be used for both ventricular and atrial cardiac mapping.

FIG. 1 is a diagram illustrating an electro-anatomical mapping system 20 for mapping cardiac rhythms of a patient 22 using intracardiac EGM signals for beat detection and processing, according to embodiments described in the disclosure. The system 20 can be operated by a user 24, such as a physician and/or a technician.

The system 20 includes one or more catheters 26, each having one or more electrodes situated at or toward the distal end of the catheter 26. The one or more catheters 26 can be situated in or near the heart of the patient 22. The system 20 obtains intracardiac EGM signals from the one or more electrodes on the catheters 26. In some embodiments, the one or more catheters 26 include one or more reference catheters, where each of the reference catheters includes one or more electrodes and is secured in place in a stable position in or near the heart. In some embodiments, the one or more catheters 26 include up to five reference catheters, each having one or more electrodes and being secured in place in a stable position in or near the heart. In some embodiments, the one or more reference catheters include at least one coronary sinus catheter.

In some embodiments, the one or more catheters 26 include one or more mapping catheters, where each of the mapping catheters includes one or more electrodes and can be moved from one location to another in the heart. In embodiments that include the one or more mapping catheters, at least one of the mapping catheters can be displaced to multiple locations within the heart during the signal acquisition stage of a mapping procedure, where the acquisition of signals at multiple catheter locations in the heart chamber enables the one or more mapping catheters to effectively act as a "mega-catheter" whose effective number of electrodes and electrode span is proportional to the product of the number of locations in which signal acquisition is performed and the number of electrodes on the one or more mapping catheters. In some embodiments, the one or more mapping catheters are configured for contact mapping. In some embodiments, the one or more mapping catheters are configured for near-contact mapping. In some embodiments, the one or more mapping catheters are configured for non-contact mapping. In some embodiments, the electrodes are mounted on the one or more mapping catheters following a three dimensional olive shape, where the electrodes are mounted on a device capable of deploying the electrodes into the desired shape while inside the heart and capable of retracting the electrodes when the catheter is removed from the heart. In embodiments, to allow deployment into the three dimensional shape, the electrodes may be mounted on a balloon or shape memory material, such as Nitinol.

In some embodiments of mapping, to enhance the quality of the physiological information at the endocardium surface, the one or more mapping catheters are moved to more than three locations, such as more than 5, 10, or even 50 locations within the heart chamber. Further, the spatial range over which the one or more mapping catheters are moved may be larger than one third (⅓) of the diameter of the heart cavity, such as larger than 35%, 40%, 50% or even 60% of the diameter of the heart cavity.

The one or more electrodes on the one or more catheters 26 receive intracardiac EGM signals resulting from electrical activity in the heart cavity. The intracardiac EGM signals are used in the beat detection and processing process and can provide, to the user 24, physiological data pertaining to the heart's electrical activity. In some embodiments, the physiological information is computed based on signals measured over several heart beats, either at a single catheter location within the heart chamber or over several locations. In embodiments where physiological information is based on multiple measurements over several heart beats, the measurements can be synchronized with one another so that the measurements are performed, and/or analyzed, with respect to approximately the same phase of the heart cycle. Also, the signal measurements over multiple beats can be synchronized based on features detected from physiological data, such as, for example, a surface electrocardiogram (ECG) or the intracardiac EGM signals.

The system 20 includes a processing unit 28, which may be, or include, a processor that executes code stored in internal memory 30 and/or in a storage device 32 to perform operations pertaining to embodiments of a mapping procedure. The internal memory 30 and/or the storage device 32 also, or alternatively, may store data acquired by the one or more electrodes of the one or more catheters 26. In some embodiments, the processing unit 28 is an electronic processor, which may be, at least in part, a software processor.

The processing unit 28 is communicatively coupled to the one or more catheters 26 and receives the intracardiac EGM signals from the one or more electrodes on the one or more catheters 26. The processing unit 28 executes code from memory, such as the internal memory 30 and/or the storage device 32, to process the intracardiac EGM signals for beat detection and processing, including beat detection, beat comparison, and beat classification for the cardiac rhythm.

In beat comparison, the processing unit 28 executes code to preprocess the intracardiac EGM signals and provide preprocessed signals, where each of the intracardiac EGM signals is preprocessed to provide a corresponding preprocessed signal. Also, the processing unit 28 executes code to compare the preprocessed signals to another set of preprocessed intracardiac EGM signals and determine a degree of similarity between each of the preprocessed signals and the other set of preprocessed intracardiac EGM signals. This degree of comparison can be used as a metric for determining how closely the signals compare to or match an existing cardiac map configuration, for acceptance of the detected beat into a map dataset, and for classification of the detected beat into a cardiac rhythm morphology. In some embodiments, to compare the preprocessed signals to another set of preprocessed signals, the processing unit 28 executes code to correlate the preprocessed signals to the other set of preprocessed intracardiac EGM signals and determines a degree of correlation between each of the preprocessed signals and the other set of preprocessed intracardiac EGM signals, where this degree of correlation can be used as a metric for determining how closely the signals compare to or match an existing cardiac map configuration, for acceptance of the detected beat into a map dataset, and for classification of the detected beat into a cardiac rhythm morphology.

In embodiments, the one or more catheters 26 include one or more reference catheters secured in place at stable locations in the patient's body, where the intracardiac EGM signals are obtained from the one or more reference catheters and the other set of preprocessed intracardiac EGM signals is a template of preprocessed intracardiac EGM signals that were determined from intracardiac EGM signals previously received by the one or more reference catheters. In some embodiments, the one or more catheters 26 include one or more mapping catheters positioned in the patient's heart, where the intracardiac EGM signals are obtained from the one or more mapping catheters and the other set of signals is a set of intracardiac EGM signals obtained from the one or more mapping catheters from a previously detected beat of the heart, such as the most recent previously detected beat of the heart.

In embodiments, the processing unit 28 executes code to determine whether to accept the intracardiac EGM signals into a cardiac map based on the degree of similarity, which in some embodiments is a degree of correlation. In embodiments, the processing unit 28 executes code to classify the intracardiac EGM signals for inclusion in a current existing cardiac map, another existing cardiac map, or a new cardiac map.

Thus, the processing unit 28 executes code from memory to process the intracardiac EGM signals with beat detection, beat comparison, and beat classification criteria for existing cardiac mapping configurations that may include existing cardiac mapping configurations that correspond to the current existing cardiac map and other existing cardiac maps. This provides information about how well the signals match the cardiac rhythm of the existing cardiac mapping configurations.

According to embodiments, the processing unit 28 executes a reconstruction procedure to determine the physiological information at the endocardium surface. To expedite embodiments of computational operations performed by the system 20, the processing unit 28 may compute, prior to the insertion of the catheter 26 into the heart chamber and/or before signal acquisition by the catheter's electrodes has commenced, transformation functions that can be used, during a mapping procedure, to facilitate the reconstruction process. After one or more catheters 26 have been inserted and displaced to a particular location in the heart chamber, the mapping procedure may be performed expeditiously by computing those transformation components that were not computed ahead of the signal acquisition stage, and combining those components with the appropriate pre-processed transformation components to obtain the overall transformation function(s). The overall transformation function may be applied to the acquired raw data to perform an inverse reconstruction operation.

The processing unit 28 may also perform a catheter registration procedure. The location of the one or more catheters 26 in the heart chamber may be determined using a conventional sensing and tracking system (not shown) that provides the three dimensional spatial coordinates of the one or more catheters 26 and/or its multiple electrodes with respect to the catheter's coordinate system as established by the sensing and tracking system. However, to perform the mapping procedure and/or reconstruct physiological information on the endocardium surface, it may be desirable to align the coordinate system(s) of the one or more catheters 26 with the endocardium surface's coordinate system. The processing unit 28 or another processing module of the system 20 may be configured to determine a coordinate system transformation function that transforms the three dimensional spatial coordinates of the catheter's locations into coordinates expressed in terms of the endocardium surface's coordinate system, or vice-versa. In some embodiments, the processing unit 28 performs post-processing operations on the reconstructed physiological information to extract and display useful features of the information to the operator of the system 20 and/or other persons, such as a physician.

The intracardiac EGM signals acquired by the one or more electrodes of the one or more catheters 26 may be passed to the processing unit 28 via a signal conditioning module 34 that receives the signals from the one or more catheters 26 and performs signal enhancement operations on the signals before they are forwarded to the processing unit 28. Signal conditioning hardware may be used to amplify, filter, and continuously sample intracardiac potential measured by one or more electrodes. In some embodiments, for example, the intracardiac signals have maximum amplitudes of 60 mV and mean amplitudes of a few millivolts. In some embodiments the signals are bandpass filtered in a frequency range, such as 0.5-500 Hz, and sampled with analog to digital converters, such as converters with 15-bit resolution at 1 kHz.

To avoid interference with electrical equipment in the room, the signals may be filtered to remove one or more frequencies corresponding to the equipment. Other types of signal processing operations may be implemented, such as, for example, spectral equalization, automatic gain control, and/or the like. The resultant processed signals are forwarded by the module 34 to the processing unit 28 for further processing.

The system 20 includes a user interface 36 and, optionally, peripheral devices, such as a printer 38, which are communicatively coupled to the processing unit 28. The user interface 36 includes one or more display devices 40 and input devices, such as a mouse 42 and a keyboard 44. The user interface 36 may receive signals from the processing unit 28 and display information about which of the existing cardiac mapping configurations more closely matches or compares to the cardiac beat, including information about whether the beat more closely matches the cardiac rhythm that corresponds to the current map or the cardiac rhythm that corresponds to a different one of the existing cardiac maps. In some embodiments, with the user interface 32 displaying this information, the user 24 can quickly and easily determine whether to add the cardiac beat into the current existing cardiac map or another one of the existing cardiac maps. In some embodiments, the user interface 36 displays this information while the system 20 is adding signals into the current map. In some embodiments, the user interface 36 includes a graphical user interface that includes a touch screen, which can be used for switching from adding beats to the current map to adding beats to another one of the existing maps or a new cardiac map.

Figure 2:
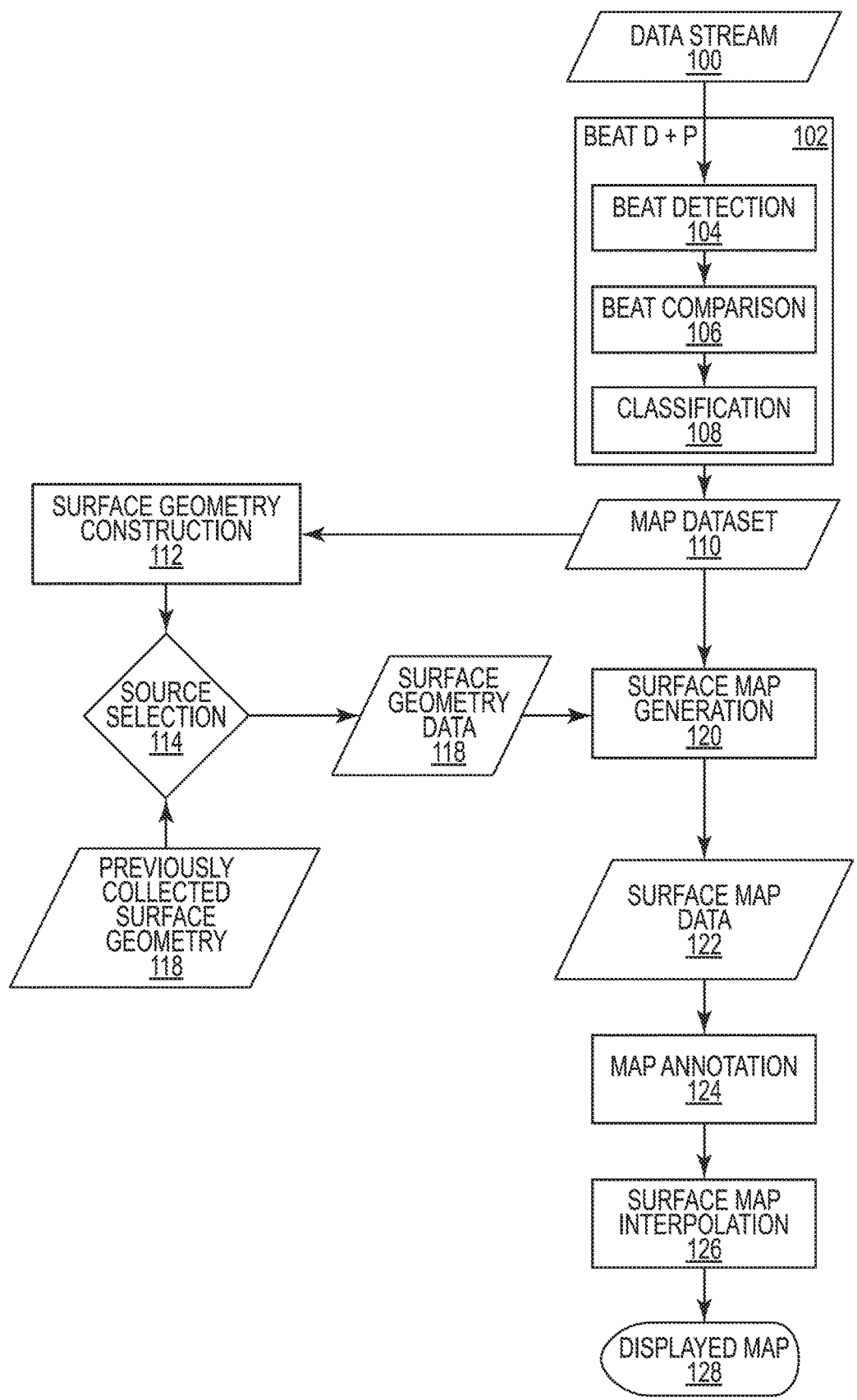
FIG. 2 is a flowchart diagram illustrating an electro-anatomical mapping process, according to embodiments of the disclosure.

FIG. 2 is a flowchart diagram illustrating an electro-anatomical mapping process, according to embodiments of the disclosure. The electro-anatomical mapping process of FIG. 2 may be performed, at least in part, by the electro-anatomical mapping system 20 of FIG. 1. In some embodiments, the processing unit 28 executes computer code stored in the internal memory 30 and/or storage device 32 to facilitate the electro-anatomical mapping process of FIG. 2.

In the electro-anatomical mapping process of FIG. 2, a data stream 100 containing multiple signals is input into the system (e.g., the mapping system 20 depicted in FIG. 1). The data stream 100 provides a collection of physiological and non-physiological signals and information that serve as inputs to the mapping process. The data stream 100 includes signals, such as unipolar or bipolar intracardiac EGM signals, received from one or more electrodes on the one or more catheters 26. Also, the data stream 100 can include signals and/or information, such as ECG signals, electrode and/or catheter location information originating from a variety of methodologies including magnetic, impedance, ultrasound, fluoroscopy, and real time magnetic resonance imaging (MRI) methodologies, tissue proximity information, catheter force or contact information such as from force spring sensing, piezo-electric sensing, and optical sensing, catheter tip and/or tissue temperature, acoustic information, catheter electrical coupling information, respiration phase, blood pressure, and/or other physiological information. In addition, the data stream 100 can contain information such as catheter shape and electrode properties. The signals and information can be collected directly by the mapping system and/or obtained from another system using an analog or digital interface.

A beat detection and processing process 102 receives the data stream 100 and processes the data to compare the data to existing cardiac mapping configurations for different beat morphologies, to accept the data into an existing map dataset, and/or to classify the data into one or more cardiac beat morphologies. The beat detection and processing process 102 can provide information for determining whether the signals in the data stream 100 should be added to the current map, added to another existing cardiac map, or added to a new cardiac map. The beat detection and processing process 102 includes a beat detection process 104, a beat comparison process 106, and a beat classification process 108.

The beat detection and processing process 102 processes the data with beat detection and beat acceptance criteria to provide information about how well the signals compare to existing cardiac mapping configurations. The beat detection and processing process 102 can process the data with beat detection and beat acceptance criteria for the current map of the existing maps into which data are currently being added, and with beat detection and beat acceptance criteria for one or more other existing maps. In some embodiments, the beat detection and processing process 102 processes the data with beat detection and beat acceptance criteria for all existing cardiac mapping configurations. In some embodiments, the beat detection and processing process 102 processes the data with beat detection and beat acceptance criteria for a subset of all existing cardiac mapping configurations. In some embodiments, the beat detection and processing process 102 continuously (or continually) processes the data or signals with beat detection and beat acceptance criteria, such as by sequentially comparing different criteria to the incoming data.

In some embodiments, the beat detection and processing process 102 displays the degree of similarity or matching between the incoming data and the existing cardiac mapping configurations via a user interface, such as the user interface 36. The beat detection and processing process 102 may display the degree of similarity for determining whether the cardiac rhythm of an existing cardiac mapping configuration more closely matches the incoming data. With this information displayed on the user interface, the user may quickly and easily determine whether the incoming data should be added to the current map, or added to another existing map or added to a new cardiac map. In some embodiments, the beat detection and processing process 102 displays at least some of the above information on the user interface while adding the incoming data to the current map.

The beat detection process 104 includes triggering from one or more signals in the data stream 100 via a trigger event, defining a window about the trigger event, and providing a matrix of signal names and signal samples from the window. One or more of the signals in the data stream 100 can be used as a reference signal for triggering relative to the cardiac rhythm of the incoming data. The beat detection process 104 detects a trigger event around which a window of data is sampled from the data stream 100. These samples, from the window of data, are put into the matrix of signal names and signal samples and provided in a beat dataset for the trigger event. In some embodiments, the trigger event is detected from one or more intracardiac EGM signals designated as a reference signal. In some embodiments, waveform attributes such as minimum/maximum, absolute maximum, maximum/minimum slope, and/or first deviation from baseline are used to detect a trigger event. In some embodiments, a single signal source can be selected for triggering, such as a single intracardiac EGM signal from one electrode on the one or more catheters 26. Also, in some embodiments, multiple intracardiac EGM signals can be used to determine a trigger event, which can be advantageous as more stable than triggering schemes based on a single signal.

In addition, in some embodiments, when aggregating data from multiple cardiac beats to create an electro-anatomical map, such as an activation map, it may be useful to trigger based on a stable reference that can provide alignment across beats to a desired phase in the cardiac cycle. While, in other embodiments, when aggregating data for another result, such as constructing an anatomical shell, one or more of the signals in the incoming data stream 100 can be used as a reference for triggering and alignment of the data stream 100 relative to a biological cycle other than the cardiac rhythm and/or to a system clock.

In response to a trigger event, the beat detection process 104 provides a beat dataset that includes the matrix of signal names and signal samples from the window of data around the trigger event for the beat dataset. Each of the signal names in the matrix is referred to as a signal channel, i.e., a channel. The beat datasets are received by the beat comparison process 106 that determines metrics for each of the beat datasets. These metrics can be used to: compare a beat dataset to an existing cardiac mapping configuration; make a decision about whether to accept a beat dataset into a map dataset 110 for the current existing cardiac map, another existing cardiac map, or a new cardiac map; and/or classify the beat dataset into a certain cardiac rhythm morphology.

The beat comparison process 106 includes a preprocessing process and a comparison process, which in some embodiments is a correlation process. In the preprocessing process, the intracardiac EGM signals are converted or transformed into preprocessed signals, where each of the intracardiac EGM signals is preprocessed to provide a corresponding preprocessed signal. The comparison process receives the preprocessed signals and compares the preprocessed signals to another set of preprocessed intracardiac EGM signals to determine the degree of similarity between each of the preprocessed signals and the other set of preprocessed intracardiac EGM signals. Comparison values determined in the comparison process can be used as beat metrics. In some embodiments, the comparison process includes a correlation process that receives the preprocessed signals and correlates the preprocessed signals to another set of preprocessed intracardiac EGM signals to determine the degree of correlation between each of the preprocessed signals and the other set of preprocessed intracardiac EGM signals, where the correlation values determined in the correlation process can be used as beat metrics. In other embodiments, the comparison process includes a different process, other than correlation, that is used to compare the preprocessed signals to another set of preprocessed intracardiac EGM signals to determine the degree of similarity between each of the preprocessed signals and the other set of preprocessed intracardiac EGM signals. In some embodiments, the one or more catheters 26 can include one or more reference catheters secured in place at stable locations in the patient's body, where the intracardiac EGM signals are obtained from the one or more reference catheters and the other set of preprocessed intracardiac EGM signals is a template of preprocessed intracardiac EGM signals that were previously received via the one or more reference catheters and preprocessed to form the template. In other embodiments, the one or more catheters 26 include one or more mapping catheters positioned in the patient's heart, where the intracardiac EGM signals are obtained from the one or more mapping catheters and the other set of signals is a set of intracardiac EGM signals obtained from the one or more mapping catheters from a previously detected beat of the heart.

In some embodiments, a number of beat metrics are computed for each of the beat datasets. These beat metrics can be computed using information from a single signal spanning one or more beats, over multiple signals within the same beat, and/or from multiple signals spanning multiple beats. The beat metrics provide multiple types of information on the quality of a beat dataset and the likelihood that the beat data in the beat dataset is acceptable for inclusion in a map dataset 110.

After the beat metrics are computed, the classification process 108 aggregates the metrics and determines which of the existing cardiac mapping configurations more closely compares to or matches the beat dataset and whether the beat dataset can be added to one of the existing map datasets 110. The classification process 108 can classify the beat datasets for acceptance into map datasets 110 for the current existing cardiac map, other existing cardiac maps, or a new cardiac map based on the degree of similarity. The classification process 108 can indicate the degree of similarity between the incoming data stream 100 and the existing cardiac mapping configurations, including the existing cardiac mapping configurations that correspond to the current map and at least one other existing cardiac map. A user, (e.g., user 24), and/or the system (e.g., system 20) may determine, based at least in part on the degree of similarity, whether to continue adding data to the current map or to switch to adding data into another one of the existing maps or a new cardiac map. In some embodiments, for example, the beat detection and processing process 102 indicates the degree of similarity between the incoming data and at least two of the existing cardiac mapping configurations, including the existing cardiac mapping configuration that corresponds to the current map, by displaying the percentage of beat datasets that are accepted and can be added into each of the different map datasets 110 over a predetermined period of time.

The electro-anatomical mapping process of FIG. 2 continues with a surface map generation process 120 that is employed to generate surface map data from the map datasets 110 and surface geometry data 118. In some embodiments, the surface geometry data 118 may be generated concurrently, or at least during the same data acquisition process, using identical or different triggering and beat acceptance metrics employing a surface geometry construction process 112. The surface geometry construction process 112 may construct surface geometry using data such as electrode locations and catheter shape contained in the data stream 100. Also, previously collected surface geometry 116 may be used as an input to the surface map data. Such surface geometry 116 may be collected in the same procedure using a different map dataset or using a different modality such as CT, MRI, ultrasound, and/or rotational angiography, and/or registered to the catheter locating system.

A system, such as system 20, may select the source of the surface geometry data at 114 and provide surface geometry data 118 to the surface map generation process 120. The surface map generation process 120 generates surface map data 122 that can provide information on cardiac electrical excitation, cardiac motion, tissue proximity information, tissue impedance information, force information, and/or any other collected and/or derived information. Once obtained, the surface map data 122 may be further processed to annotate desired features from the underlying data, a process defined herein as surface map annotation 124. Desired annotations may include instantaneous potential, activation time, voltage amplitude, dominant frequency and/or other properties of the signal. Once computed, the annotations may be displayed superimposed on chamber geometry. If the number of annotations is lower than the number of elements that make up the display of surface geometry, surface map interpolation 126 may be employed. Displayed maps 128 may be computed and displayed separately, combined, and/or overlaid on top of each other.

Figure 3:
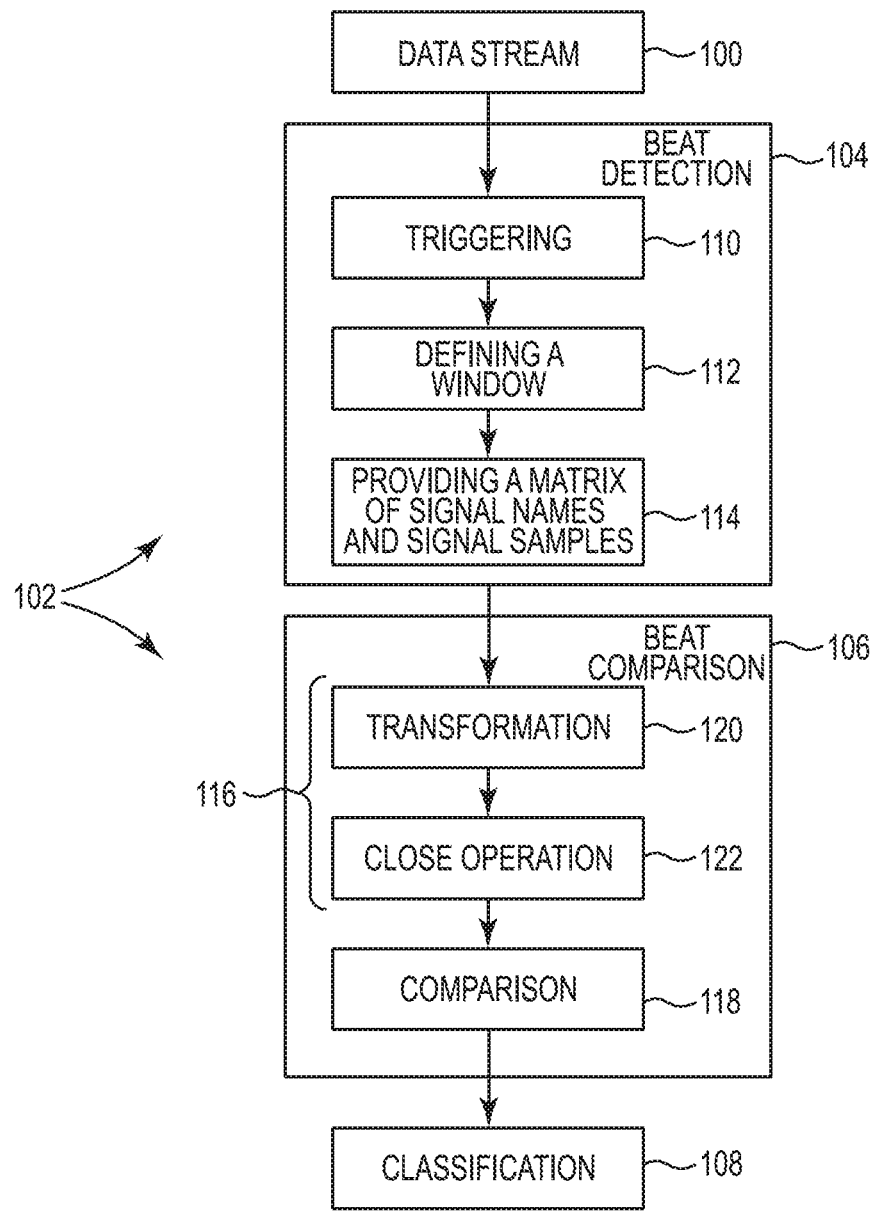
FIG. 3 is a flowchart diagram illustrating a data stream and a beat detection and processing process, according to embodiments of the disclosure.

FIG. 3 is a flowchart diagram illustrating the data stream 100 and the beat detection and processing process 102, according to embodiments of the disclosure. The beat detection and processing process 102 includes the beat detection process 104, the beat comparison process 106, and the beat classification process 108, as shown in FIG. 2 and described in the description of FIG. 2. The beat detection and processing process 102 processes the data stream 100 to provide information about how closely the signals in the data stream 100 compare to existing cardiac mapping configurations. In some embodiments, the beat detection and processing process 102 processes the data with existing cardiac mapping configurations, including beat detection and beat acceptance criteria, for the current map and one or more other existing maps for determining whether the signals in the data stream 100 should be added to the current map, added to another existing cardiac map, or added to a new cardiac map.

The beat detection process 104 receives the data stream 100 and provides triggering 110 of the data stream 100 via a trigger event, defining a window 112 about the trigger event, and providing a matrix of signal names and signal samples 114 from the window, where each of the signal names in the matrix is referred to as a signal channel, i.e., a channel.

In triggering 110, the beat detection process 104 identifies a trigger event, such as an activation of a cardiac rhythm in the heart, in the data stream 100. The trigger event indicates when a beat occurs and is detected in the data stream 100 using one or more of the signals or channels in the data stream 100 as a reference signal or channel. In some embodiments, the trigger event is detected from one or more intracardiac EGM signals or channels designated as a reference signal or channel. In some embodiments, waveform attributes such as minimum/maximum, absolute maximum, maximum/minimum slope, and/or first deviation from baseline are used to detect a trigger event. In some embodiments, a single signal source can be selected for triggering, such as a single intracardiac EGM signal or channel from one electrode on the one or more catheters 26. In some embodiments, multiple intracardiac EGM signals or channels can be used to determine a trigger event. In some embodiments, triggering 110 identifies activations in an atrium of the heart. In some embodiments, triggering 110 identifies activations in a ventricle of the heart. In some embodiments, schemes, such as beat blanking, are used to enhance identification of a trigger event and a beat.

In defining a window 112, the beat detection process 104 defines a window in time around or about the trigger event. The window identifies the part of the beat that may be useful in determining cardiac rhythm morphology and other characteristics about the beat. In some embodiments, the window size can be 100-300 milliseconds long.

In providing a matrix of signal names (channels) and signal samples 114, the beat detection system 104 samples at least some of the intracardiac EGM signals in the data stream 100 during the window to obtain a number of samples for each of the signals. The names of the signals sampled (the channels) and the samples are put into a matrix of signal names and signal samples and provided in a beat dataset for the trigger event. In some embodiments, the signals can be sampled at a predetermined sampling rate. In some embodiments, the sampling rate is 1 KHz. In some embodiments, the number of samples is from 100-300 samples Thus, in response to the trigger event, the beat detection process 104 provides a beat dataset that includes the matrix of signal names and signal samples from the window of data around the trigger event. The beat datasets are received by the beat comparison process 106 that determines beat metrics for each of the beat datasets. These beat metrics can be used to: compare a beat dataset to an existing cardiac mapping configuration; make a decision about whether to accept a beat dataset into a map dataset 110 for the current existing cardiac map, another existing cardiac map, or a new cardiac map; and/or classify the beat dataset into a certain cardiac rhythm morphology.

The beat comparison process 106 includes preprocessing 116 of the matrix of signal names and signal samples into preprocessed signals and comparison 118 of the preprocessed signals to other preprocessed signals. The preprocessing 116 includes transformation 120 of the signals in the matrix into transformed signals and a close operation 122 on the transformed signals. In some embodiments, the comparison 118 includes correlation of the preprocessed signals to other preprocessed signals.

In transformation 120, the intracardiac EGM signals in the matrix are converted or transformed into transformed signals. Each of the intracardiac EGM signals is converted or transformed into a corresponding transformed signal. In some embodiments, the transformation 120 includes applying a Hilbert transform on each of the intracardiac EGM signals to provide a corresponding transformed signal. Using the Hilbert transform, the magnitude of the signal, which is a local estimate of power, is computed, where each of the transformed signals is substantially an envelope of the power in the signal. In other embodiments, another type of transform or conversion can be used to show signal content and amplitude.

In the close operation 122, a noise reduction operation is performed on each of the transformed signals to provide preprocessed signals. The noise reduction operation reduces noise, fills in gaps, and/or removes artifacts in the transformed signals to provide the preprocessed signals. In some embodiments, the close operation includes a morphological close operation. In some embodiments, the close operation includes shape preserving morphological noise reduction to reduce sensitivity to subtle signal variations. In some embodiments, the close operation includes shape preserving morphological noise reduction using a plus or minus 5 millisecond greyscale. In some embodiments, the close operation 122 is similar to an image processing operation for removing noise, filling in gaps, and/or removing artifacts. In some embodiments, the close operation 122 is a non-boolean close operation.

Optionally, the close operation 122 includes bandpass filtering of the signals for frequency selectivity. The output of the close operation 122 is a preprocessed signal, also referred to as an activation waveform, which is provided for metric computational stages and/or template production.

The comparison process 118 receives the preprocessed signals from the close operation 122 and compares the preprocessed signals to another set of preprocessed intracardiac EGM signals to determine a degree of similarity between each of the preprocessed signals and the other set of preprocessed intracardiac EGM signals. The comparison values determined in the comparison process 118 are used as beat metrics that indicate how closely the preprocessed signals, and the beat dataset from which they came, compare to or match the beat morphology or cardiac rhythm shape represented by the other set of preprocessed intracardiac EGM signals. In some embodiments, the comparison process 118 compares the preprocessed signals to multiple other sets of preprocessed intracardiac EGM signals to determine a degree of similarity between the preprocessed signals and each of the other sets of preprocessed intracardiac EGM signals and their cardiac rhythm shapes.

In some embodiments, the comparison process 118 includes a correlation process that receives the preprocessed signals from the close operation 122 and correlates the preprocessed signals to another set of preprocessed intracardiac EGM signals to determine a degree of correlation between each of the preprocessed signals and the other set of preprocessed intracardiac EGM signals. The correlation values determined in the correlation process are used as beat metrics that indicate how closely the preprocessed signals, and the beat dataset from which they came, compare to or match the beat morphology or cardiac rhythm shape represented by the other set of preprocessed intracardiac EGM signals.

In some embodiments, the intracardiac EGM signals are obtained from one or more reference catheters and the other set of preprocessed intracardiac EGM signals is a template of preprocessed intracardiac EGM signals. Where, the template represents one beat morphology or cardiac rhythm shape and the intracardiac EGM signals used to form the template are received via the one or more reference catheters and preprocessed to form the template. In some embodiments, the comparison process 118 compares the preprocessed signals to one or more templates to determine the degree of similarity between the preprocessed signals and each of the one or more templates and their cardiac rhythm shapes.

In other embodiments, the intracardiac EGM signals are obtained from one or more mapping catheters and the other set of signals is a set of intracardiac EGM signals obtained from the one or more mapping catheters from a previously detected beat of the heart, such as the most recent previously detected beat of the heart.

After the comparison values are computed, the classification process 108 aggregates the comparison value metrics and determines which of the existing cardiac mapping configurations more closely compares to the beat dataset and whether the beat dataset can be added to one of the existing map datasets 110. The classification process 108 can classify the beat datasets for acceptance into map datasets 110 for the current existing cardiac map, other existing cardiac maps, or a new cardiac map based on the degree of similarity. In some embodiments, the comparison values are determined for multiple templates and the classification process 108 classifies the beat dataset for adding to map datasets 110 for the current existing cardiac map, other existing cardiac maps, and/or a new cardiac map based on the comparison values.

Figure 4:
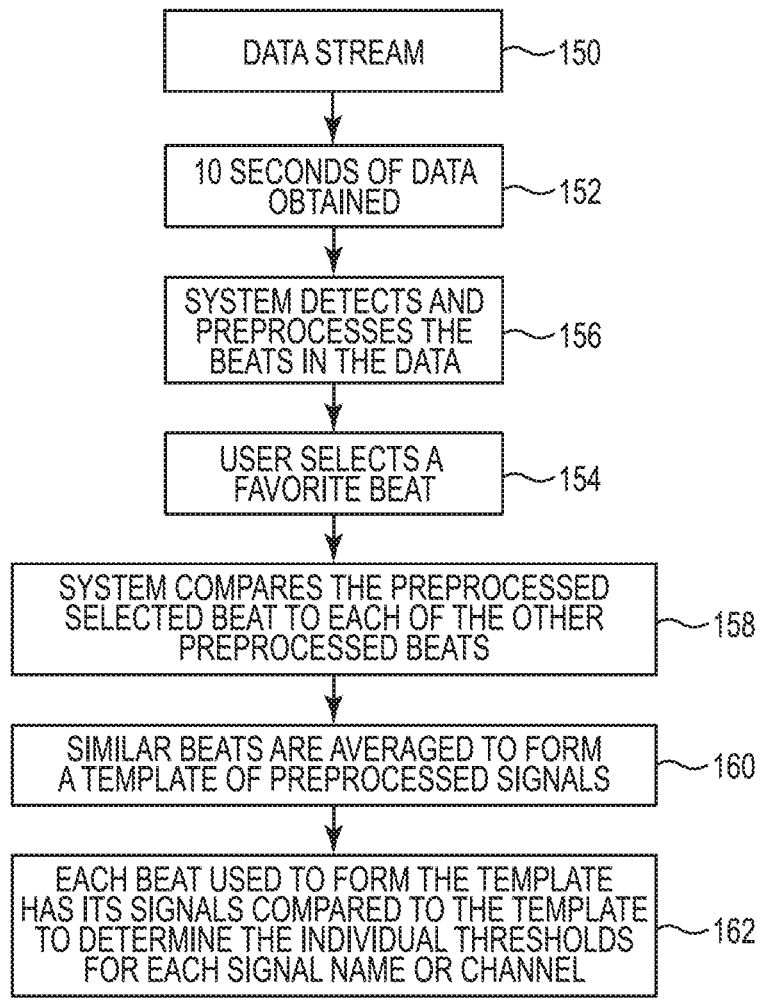
FIG. 4 is a flowchart diagram illustrating formation of a template of preprocessed intracardiac EGM signals that can be used in a comparison process, according to embodiments of the disclosure.

FIG. 4 is a flowchart diagram illustrating the formation of a template of preprocessed intracardiac EGM signals, which can be used in the comparison process 118, according to embodiments of the disclosure. The preprocessed intracardiac EGM signals to be compared to the template in the comparison process 118 are obtained via one or more reference catheters situated in stable positions in or near the heart. Thus, to form the template, the data stream 150 includes intracardiac EGM signals obtained from the same one or more reference catheters.

At 152, 10 seconds of data is obtained from the data stream 150. This 10 seconds of data contains a number of beats of the heart, such as 10 to 15 beats.

At 154, a system, such as system 20, detects and preprocesses the beats in the 10 seconds of data. At this step, each of the intracardiac EGM signals of interest in each of the beats is preprocessed to provide a corresponding preprocessed signal. In some embodiments, the system uses the beat detection process 104 and the preprocessing 116 from the beat comparison process 106 to detect beats and preprocess the signals at 154.

At 156, a user, such as a physician or a technician, selects one of the beats in the 10 seconds of data as a favorite beat, where the favorite beat often represents a cardiac rhythm morphology that the user wants to map.

At 158, the system compares the preprocessed signals of the favorite beat to the preprocessed signals of the other beats. At this step, each of the preprocessed intracardiac EGM signals from the favorite beat is compared to each of the corresponding preprocessed intracardiac EGM signals from the other preprocessed beats. A beat is considered similar to the favorite beat if the signals in the beat compare favorably to the signals in the favorite beat. The corresponding signals in the similar beats are averaged together to form averaged signals in the template. In some embodiments, the preprocessed intracardiac EGM signals from the selected beat are correlated to the preprocessed intracardiac EGM signals from the other preprocessed beats. In some embodiments, a beat is considered similar to the favorite beat if all reference signals or channels in the beats have a minimum correlation value of greater than or equal to 0.8.

At 160, the beats that are deemed to be similar beats are averaged to form a template of preprocessed signals. At this step, each of the preprocessed intracardiac EGM signals is averaged with the corresponding preprocessed intracardiac EGM signals of other similar beats to obtain average signals for each of the preprocessed intracardiac signals in the template.

At 162, after forming the template, each beat that was used to form the template has its signals compared to the averaged signals in the template to determine individual threshold values for each of the signal channels. These individual thresholds are confidence levels that indicate the amount of information in and the confidence a user can have in a particular channel. At this step, in some embodiments, each of the preprocessed intracardiac EGM signals of a beat used to form the template is correlated to each of the corresponding averaged preprocessed intracardiac EGM signals in the template to obtain the individual thresholds. In some embodiments, an individual threshold for each of the signal channels is determined based on the minimum cross correlation coefficient between the averaged signal of the template and the corresponding signals of each of the similar beats used to form the template, as indicated in Equation I:

$$\theta_{o,j} = \min[\overline{V}_j \otimes V_{i,j}]$$

where $\theta_{o,j}$ is the individual threshold for channel j, $V_{i,j}$ is the waveform or signal from channel j of similar beat i, $\overline{V}_j$ is channel j of the template, and $\otimes$ is the cross correlation operator.

Figure 5:
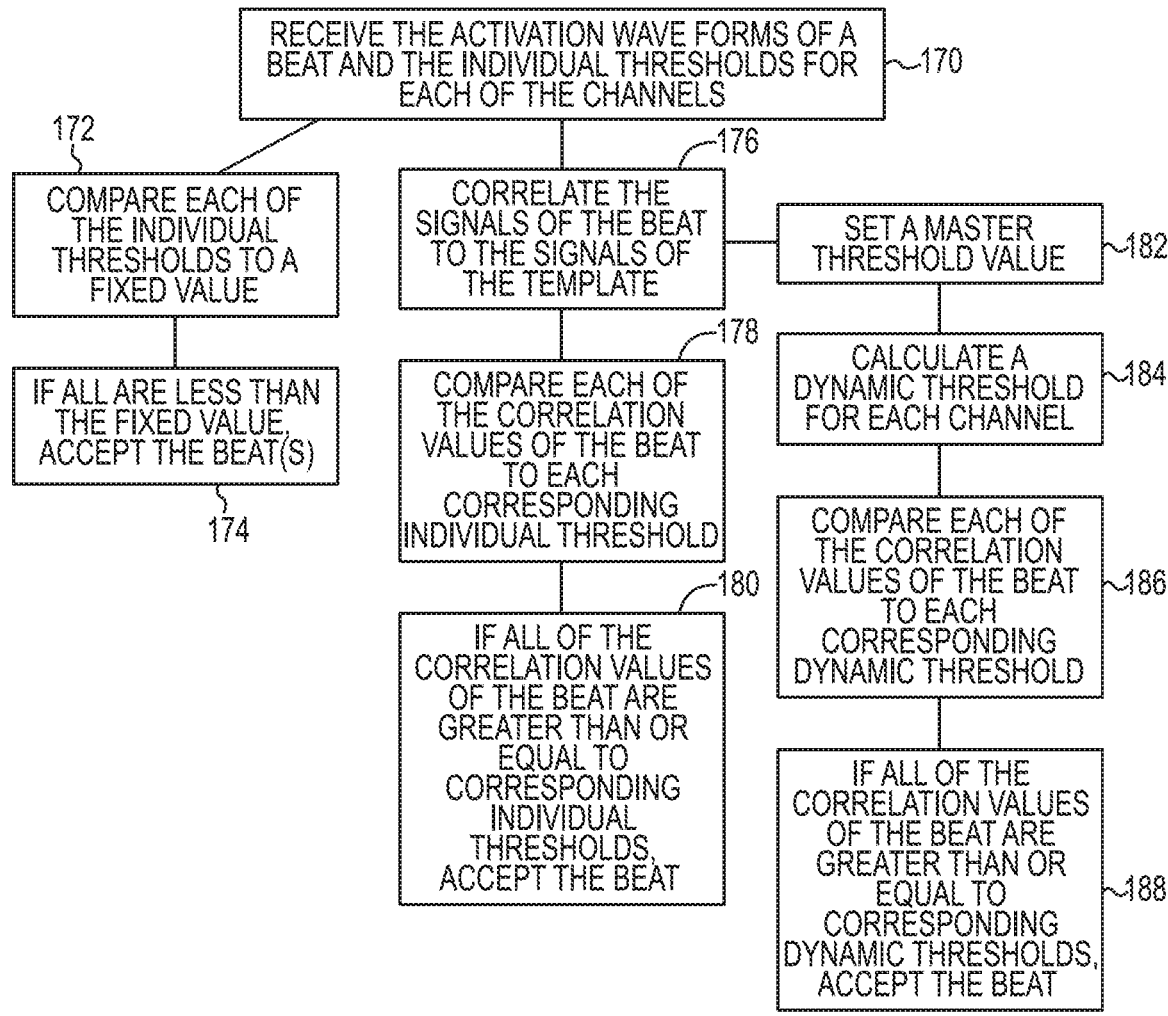
FIG. 5 is a flowchart diagram illustrating a comparison process, according to embodiments of the disclosure.

FIG. 5 is a flowchart diagram illustrating a comparison process 118, according to embodiments of the disclosure. The comparison process 118 includes a correlation process and acceptance/rejection criteria for correlating preprocessed intracardiac EGM signals of a beat to the averaged preprocessed intracardiac EGM signals of a template and determining whether to accept or reject the beat as matching the template. The intracardiac EGM signals of the beat were obtained via one or more reference catheters and the intracardiac EGM signals used to form the template were also obtained via the one or more reference catheters. Also, in this example, the template is formed using the process of FIG. 4. As described above, each of the channels or signal names in the template has an individual threshold value.

At 170, the comparison process 118 receives the preprocessed intracardiac EGM signals (activation waveforms) of a beat from the close operation 122 of preprocessing 116 and the comparison process 188 receives the individual thresholds for each of the channels.

At 172, the comparison process 118 compares each of the individual thresholds to a fixed value and, at 174, if all of the individual threshold values are less than the fixed value, the beat is accepted as matching the template. If one or more of the individual threshold values is greater than the fixed value, processing can continue at 176. In some embodiments, the fixed value is zero and if the individual thresholds are all less than or equal to zero the beats are accepted as matching the template.

At 176, the comparison process 118 correlates the preprocessed intracardiac EGM signals of the beat to the averaged preprocessed intracardiac EGM signals of the template. Each of the preprocessed intracardiac EGM signals of a beat is correlated to the averaged preprocessed intracardiac EGM signals in the template to provide a correlation value for that signal of the beat. In some embodiments, other comparisons and/or correlations can be used to determine the correlation value of a signal to the template.

At 178, the comparison process 118 compares each of the correlation values of the beat to each corresponding individual threshold value for the channel and, at 180, if all of the correlation values obtained at 176 are greater than or equal to the corresponding individual threshold values, the beat is accepted as matching the template, otherwise processing can continue at 182.

At 182, after correlating the preprocessed intracardiac EGM signals of the beat to the averaged preprocessed intracardiac EGM signals of the template at 176, the comparison process 118 sets a master threshold value. The master threshold value is seen by the user 24 and can be set by the user 24 or the system 20. The master threshold value modulates each of the individual thresholds of the channels to provide a dynamic threshold value for each of the channels.

At 184, the comparison process 118 calculates a dynamic threshold value for each of the channels based on the individual threshold value for the channel and the master threshold value. In some embodiments, each of the dynamic threshold values is calculated as shown in Equation II:

$$\theta d = \breve{\theta}\alpha + (-1)(1-\alpha)$$

where, $\breve{\theta}$ is calculated as shown in Equation III, $$\breve{\theta} = \theta_0 - (1-t)$$

and $\alpha$ is calculated as shown in Equation IV, $$\alpha = \breve{\theta}^g$$

where $\theta_0$ is the individual threshold, t is the master threshold value, and g is a shape parameter with a value, in some embodiments, selected to be 0.1.

At 186, the comparison process 118 compares each of the correlation values of the beat to each corresponding dynamic threshold value for the channel and, at 188, if all of the correlation values obtained at 176 are greater than or equal to the corresponding dynamic threshold values, the beat is accepted as matching the template. If the beat is not accepted, via any of the above criteria, at 174, 180, and 188, the beat is rejected. This follows the principal that one bad or wrong signal makes the entire beat unacceptable and eliminates beats if any of the signals in the beat do not provide a correlation value that is greater than or equal to the individual threshold value or the dynamic threshold value for that channel.

In other embodiments, the dynamic threshold values can be calculated differently. In some embodiments, each of the individual threshold values can be multiplied by the master threshold value to obtain a dynamic threshold value. For example, if the master threshold level is set to 0.6, then each of the individual threshold values is multiplied by 0.6 to provide the dynamic threshold level for that particular signal name/channel.

Figure 6:
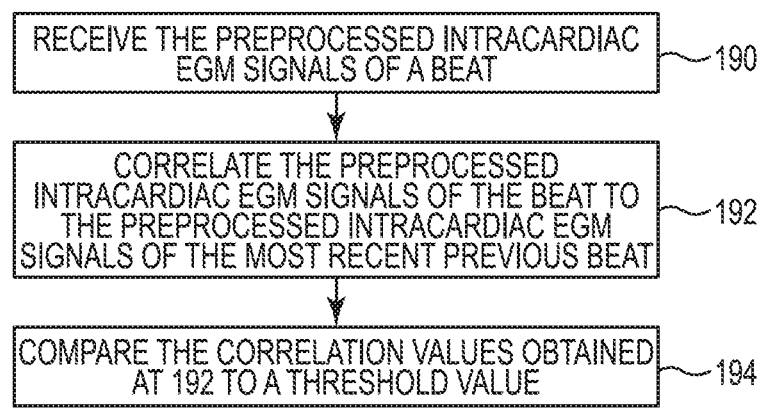
FIG. 6 is a flowchart diagram illustrating another comparison process, according to embodiments of the disclosure.

FIG. 6 is a flowchart diagram illustrating the comparison process 118 correlating preprocessed intracardiac EGM signals of a beat to a set of preprocessed intracardiac EGM signals of a previous beat, according to embodiments of the disclosure. In this example, the intracardiac EGM signals of the beat were obtained via one or more mapping catheters and the intracardiac EGM signals of the previous beat were also obtained via the one or more mapping catheters.

At 190, the comparison process 118 receives the preprocessed intracardiac EGM signals of a beat from the close operation 122 of preprocessing 116. These preprocessed intracardiac EGM signals are correlated to the preprocessed intracardiac EGM signals of the most recent previous beat to provide beat metrics for the beat. Based on these beat metrics, the beat will be either accepted or rejected as matching the most recent previous beat.

At 192, the comparison process 118 correlates the preprocessed intracardiac EGM signals of the beat to the preprocessed intracardiac EGM signals of the most recent previous beat. Each of the preprocessed intracardiac EGM signals of the beat is correlated to the set of preprocessed intracardiac EGM signals of the previous beat to obtain correlation values. In some embodiments, other comparisons and/or correlations can be used to determine the comparison value of a signal to the previous beat.

At 194, the comparison process 118 compares the correlation values obtained at 192 to a corresponding threshold value. Where, in some embodiments, the threshold value is set by the user to be between zero and one.

In some embodiments, if any of the correlation values obtained at 192 is below a corresponding threshold value for that signal name, the beat is rejected. This follows the principal that one bad or wrong signal makes the entire beat unacceptable and eliminates beats from mapping if any of the signals in the beat do not correlate to the previous beat to provide a correlation value that is greater than or equal to the corresponding threshold value.

Figure 7:
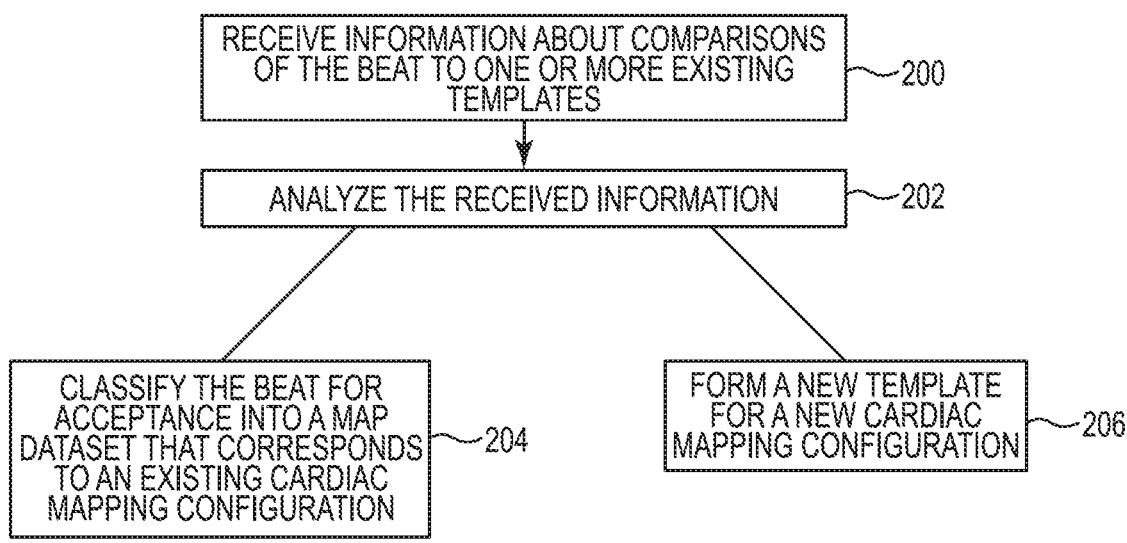
FIG. 7 is a flowchart diagram illustrating a classification process, according to embodiments of the disclosure.

FIG. 7 is a flowchart diagram illustrating the classification process 108, according to embodiments of the disclosure. The classification process 108 aggregates the metrics and determines which of the existing cardiac mapping configurations more closely compares to or matches the beat dataset and whether the beat dataset can be added to one of the existing map datasets 110. The classification process 108 can classify the beat datasets for acceptance into map datasets 110 for the current existing cardiac map, other existing cardiac maps, or a new cardiac map based on the degree of similarity, which in some embodiments is the degree of correlation. The classification process 108 can indicate the degree of similarity between the incoming data stream 100 and the existing cardiac mapping configurations, including the existing cardiac mapping configurations that correspond to the current map and at least one other existing cardiac map.

As described in relation to FIG. 5, the comparison process 118 compares the intracardiac EGM signals of a beat to the averaged intracardiac EGM signals of a template and provides comparison values, such as correlation values, that are used as beat metrics for the beat. Where, the template may correspond to an existing cardiac map and the map dataset 110 for that existing cardiac map. In some embodiments, the comparison process 118 compares the intracardiac EGM signals of a beat to multiple existing templates and provides multiple sets of comparison values, one set of comparison values for each comparison to a different existing template. In some embodiments, the multiple existing templates correspond to the current existing cardiac map and one or more other existing cardiac maps.

At 200, the classification process 108 receives information about the comparisons of the beat to one or more existing templates. In some embodiments, the classification process 108 receives the comparison values, such as correlation values, from the comparison process 118, for the comparisons of the beat to the different templates. In some embodiments, the classification process 108 receives acceptance/rejection determinations, from the comparison process 118, for the comparisons of the beat to the different templates.

At 202, the classification process 108 analyzes the received information about the comparisons of the beat to one or more existing templates. In some embodiments, the classification process 108 analyzes the correlation values against the individual and dynamic threshold values for the comparisons to classify the beat into one of the existing cardiac maps or to build a new cardiac map. In some embodiments, the classification process 108 analyzes the acceptance/rejection determinations from the comparison process 118 to classify the beat into one of the existing cardiac maps or to build a new cardiac map.

At 204, if the beat more closely compares to or matches one of the templates, the classification process 108 classifies the beat for acceptance into a map dataset 110 that corresponds to the template.

At 206, if the beat does not match any of the existing templates, the classification process 108 forms a new template for a new cardiac mapping configuration and classifies the beat for acceptance into a new map dataset 110 that corresponds to the new template.

A user, (e.g., user 24), and/or the system (e.g., system 20) may determine, based at least in part on the degree of similarity, whether to add the data to the current map or to switch and add the data into another one of the existing maps or to make a new cardiac map. In some embodiments, for example, the classification process 108 indicates the degree of similarity between the incoming data and at least two of the existing cardiac maps, including the current map, by displaying the percentage of beat datasets that can be added into each of the different map datasets 110 over a predetermined period of time.

Various modifications and additions can be made to the exemplary embodiments discussed without departing from the scope of the disclosure. For example, while the embodiments described above refer to particular features, the scope of this disclosure also includes embodiments having different combinations of features and embodiments that do not include all of the described features. Accordingly, the scope of the disclosure is intended to embrace all such alternatives, modifications, and variations as fall within the scope of the claims, together with all equivalents thereof.

We claim:

1. A system for providing information about a patient's heart, the system comprising:
   one or more catheters that receive intracardiac signals from electrical activity of the heart over one or more heart beat cycles; and
   an electronic processor coupled to the one or more catheters to:
   receive the intracardiac signals from the one or more catheters;
   preprocess the intracardiac signals to provide preprocessed signals, wherein each of the intracardiac signals is preprocessed to provide a corresponding preprocessed signal;
   compare the preprocessed signals to a set of signals to determine a degree of similarity between each of the preprocessed signals and the set of signals; and
   determine whether to accept one or more beats of the intracardiac signals into an existing cardiac map based on the degree of similarity,
   wherein to compare the preprocessed signals to a set of signals and determine whether to accept one or more beats, the electronic processor is configured to:
   determine a template from the preprocessed signals by comparing the preprocessed signals for each signal channel of signal channels for the set of signals from one of the heart beat cycles to the preprocessed signals for each signal channel of the signal channels from other heart beat cycles, selecting beats based on the comparison, and averaging the preprocessed signals for each signal channel of the signal channels from the selected beats to form averaged preprocessed signals for each signal channel of the signal channels in the template;
   determine an individual threshold value for each signal channel of the signal channels by comparing the preprocessed signals for each signal channel of the signal channels from each of the selected beats to the averaged preprocessed signals of each signal channel of the signal channels in the template;
   compare each of the preprocessed signals to the set of signals to obtain a comparison value for each of the signal channels; and
   compare the comparison value for each of the signal channels to the individual threshold value for each of the signal channels to determine whether a beat of the intracardiac signals is to be accepted into the existing cardiac map; and
   a display that displays a result of the comparison such that a user can switch between adding the beats of the intracardiac signal to a current cardiac map and adding the beats of the intracardiac signals to another cardiac map based on the comparison.

2. The system of claim 1, wherein to preprocess the intracardiac signals the electronic processor is to:
   apply a transform function to the intracardiac signals to provide transformed signals, wherein each of the intracardiac signals is transformed to a corresponding transformed signal; and
   apply a morphological close operation to each of the transformed signals to reduce noise in the preprocessed signals.

3. The system of claim 2, wherein the transform function is a Hilbert transform and the close operation is a non-boolean close operation.

4. The system of claim 1, wherein the electronic processor is to:
   detect a beat of the heart;
   define a window for samples of the intracardiac signals based on the beat; and
   provide a matrix of the samples of the intracardiac signals in the window.

5. The system of claim 1, wherein the one or more catheters include one or more reference catheters situated at stable positions in the patient's body.

6. The system of claim 1, wherein the one or more catheters include one or more mapping catheters positioned in the patient's heart and the set of signals includes a set of signals from the one or more mapping catheters and a previously detected beat of the heart.

7. The system of claim 1, wherein to compare the preprocessed signals the electronic processor is to:
   receive individual threshold values for each of the intracardiac signals;
   set a master threshold value;
   provide dynamic threshold values for each of the intracardiac signals based on the individual threshold values and the master threshold value;
   compare the preprocessed signals to the set of signals to obtain comparison values for the intracardiac signals; and compare the comparison values to the dynamic threshold values to determine whether a beat of the intracardiac signals is to be accepted into an existing cardiac map.

8. The system of claim 1, wherein to compare the preprocessed signals the electronic processor is to:
receive individual threshold values for each of the intracardiac signals; and
compare each of the individual threshold values to a fixed value and if all of the individual threshold values are less than the fixed value, accept one or more beats of the intracardiac signals into an existing cardiac map.

9. The system of claim 1, wherein to compare the preprocessed signals the electronic processor is to:
compare the preprocessed signals to a set of signals from one or more mapping catheters and a previously detected beat of the heart to obtain previous beat comparison values; and
compare each of the previous beat comparison values to a corresponding threshold value to determine whether a beat of the intracardiac signals is to be accepted.

10. The system of claim 1, wherein the electronic processor is to determine whether to:
classify the intracardiac signals into the current cardiac map;
classify the intracardiac signals into another existing cardiac map; or
make a new cardiac map based on the intracardiac signals.

11. A method for mapping a patient's heart, comprising:
receiving intracardiac signals from electrical activity of the heart over one or more heart beat cycles at one or more catheters;
receiving the intracardiac signals at an electronic processor that is coupled to the one or more catheters;
preprocessing the intracardiac signals, by the electronic processor, to provide preprocessed signals, wherein each of the intracardiac signals is preprocessed to provide a corresponding preprocessed signal;
comparing the preprocessed signals, by the electronic processor, to a set of signals to determine a degree of similarity between each of the preprocessed signals and the set of signals; and
determining whether to accept the intracardiac signals into an existing cardiac map based on the degree of similarity,
wherein comparing the preprocessed signals to a set of signals and determining whether to accept the intracardiac signals comprises:
determining a template from the preprocessed signals by comparing the preprocessed signals for each signal channel of signal channels for the set of signals from one of the heart beat cycles to the preprocessed signals for each signal channel of the signal channels from other heart beat cycles, selecting beats based on the comparison, and averaging the preprocessed signals for each signal channel of the signal channels from the selected beats to form averaged preprocessed signals for each signal channel of the signal channels in the template;
determining an individual threshold value for each signal channel of the signal channels by comparing the preprocessed signals for each signal channel of the signal channels from each of the selected beats to the averaged preprocessed signals of each signal channel of the signal channels in the template;
comparing each of the preprocessed signals to the set of signals to obtain a comparison value for each of the signal channels; and
comparing the comparison value for each of the signal channels to the individual threshold value for each of the signal channels to determine whether a beat of the intracardiac signals is to be accepted into the existing cardiac map; and
displaying a result of the comparison on a display such that a user can switch between adding the beats of the intracardiac signal to a current cardiac map and adding the beats of the intracardiac signals to another cardiac map based on the comparison.

12. The method of claim 11, wherein preprocessing the intracardiac signals includes:
transforming each of the intracardiac signals via a transform function; and
applying a close operation to reduce noise in the preprocessed signals.

13. The method of claim 11, wherein comparing the preprocessed signals comprises:
receiving individual threshold values for each of the intracardiac signals;
setting a master threshold value;
providing dynamic threshold values for each of the intracardiac signals based on the individual threshold values and the master threshold value;
comparing the preprocessed signals to the set of signals to obtain comparison values for the intracardiac signals; and
comparing the comparison values to the dynamic threshold values to determine whether a beat of the intracardiac signals is to be accepted into an existing cardiac map.

14. The method of claim 11, wherein comparing the preprocessed signals comprises:
receiving individual threshold values for each of the intracardiac signals; and
comparing each of the individual threshold values to a fixed value and if all of the individual threshold values are less than the fixed value, accept one or more beats of the intracardiac signals into an existing cardiac map.

15. The method of claim 11, wherein comparing the preprocessed signals comprises:
comparing the preprocessed signals to a set of signals from one or more mapping catheters and a previously detected beat of the heart to obtain previous beat comparison values; and
comparing each of the previous beat comparison values to a corresponding threshold value to determine whether a beat of the intracardiac signals is to be accepted.

* * * * *